(12) United States Patent
Truckai et al.

(10) Patent No.: US 7,306,598 B2
(45) Date of Patent: Dec. 11, 2007

(54) POLYMER MATRIX DEVICES FOR TREATMENT OF VASCULAR MALFORMATIONS

(75) Inventors: Csaba Truckai, Saratoga, CA (US); John H. Shadduck, Tiburon, CA (US)

(73) Assignee: DFINE, Inc., Cupertino, CA (US)

( * ) Notice: Subject to any disclaimer, the term of this patent is extended or adjusted under 35 U.S.C. 154(b) by 274 days.

(21) Appl. No.: 10/456,113

(22) Filed: Jun. 5, 2003

(65) Prior Publication Data

US 2003/0208192 A1 Nov. 6, 2003

Related U.S. Application Data

(60) Provisional application No. 60/386,278, filed on Jun. 5, 2002.

(51) Int. Cl.
*A61B 18/18* (2006.01)
*A61B 5/04* (2006.01)

(52) U.S. Cl. .................. 606/49; 600/395; 600/374; 606/41

(58) Field of Classification Search .......... 606/3–34, 606/41, 48–50; 600/372–374, 395–397; 607/115, 116
See application file for complete search history.

(56) References Cited

U.S. PATENT DOCUMENTS

| | | | |
|---|---|---|---|
| 3,828,780 A | 8/1974 | Morrison, Jr. | |
| 4,653,501 A * | 3/1987 | Cartmell et al. | 600/392 |
| 5,108,407 A | 4/1992 | Geremia et al. | |
| 5,330,527 A * | 7/1994 | Montecalvo et al. | 607/152 |
| 5,331,959 A * | 7/1994 | Imran | 600/383 |
| 5,507,744 A | 4/1996 | Tay et al. | |
| 5,522,836 A | 6/1996 | Palermo | |
| 5,562,720 A * | 10/1996 | Stern et al. | 607/98 |
| 5,749,894 A | 5/1998 | Engelson | |
| 5,797,903 A * | 8/1998 | Swanson et al. | 606/34 |
| 6,024,754 A | 2/2000 | Engelson | |
| 6,053,910 A * | 4/2000 | Fleenor | 606/32 |
| 6,193,708 B1 | 2/2001 | Ken et al. | |
| 6,231,573 B1 | 5/2001 | Amor et al. | |
| 6,458,127 B1 * | 10/2002 | Truckai et al. | 606/49 |
| 6,464,716 B1 * | 10/2002 | Dobak et al. | 607/105 |
| 2004/0044341 A1 | 3/2004 | Truckai et al. | |
| 2005/0267467 A1 * | 12/2005 | Paul et al. | 606/41 |

* cited by examiner

*Primary Examiner*—Michael Peffley
(74) *Attorney, Agent, or Firm*—Knobbe Martens Olson & Bear, LLP

(57) ABSTRACT

A system for treating a wide-neck aneurysm comprising a mesh-like sleeve fabricated from a class of polymer filaments that carry conductive particles therein to provide the filaments with a specified resistivity. The releasable mesh-like sleeve is introduced to the site of a targeted vascular malformation by the working end of a catheter that carries an electrode arrangement at its distal terminus. The system further provides an electrical source and controller (i) that modulates power delivery to the polymer matrix which can then fuse the sleeve to the wall of a blood vessel to span across the vascular malformation.

25 Claims, 21 Drawing Sheets

POLYMER MATRIX DEVICES FOR TREATMENT OF VASCULAR MALFORMATIONS

CROSS-REFERENCE TO RELATED APPLICATION

This application claims benefit from Provisional U.S. Patent Application Ser. No. 60/386,278 filed Jun. 5, 2002 having the same title, which application is incorporated herein by this reference.

FIELD OF THE INVENTION

This invention relates to medical systems and techniques for occluding aneurysms. More particularly, an exemplary system provides a novel type of mesh-like sleeve of a polymer microfilament that carries conductive particles therein or carries a very thin metallic surface coating. The microfilament of a polymer matrix is adapted to have a specified resistance to electrical current flow therein. The system further provides an electrical source and controller (i) that modulates power delivery to the polymer matrix which can then fuse the sleeve to the wall of a blood vessel to span across a vascular malformation.

BACKGROUND OF THE INVENTION

Various devices and techniques have been developed for occluding aneurysms or other vascular defects or deformations (herein termed malformations). A common type of aneurysm treatment utilizes a detachable coil that is fed into the aneurysm to substantially occupy the aneurysm volume. The typical approach for implanting an embolic coil in an aneurysm involves attaching the coil to the distal end of a pushwire, and introducing the pushwire and coil through a catheter lumen until the coil is pushed into the aneurysm. The typical manner of detaching the coil from the pushwire involves using a direct current to cause electrolysis of a sacrificial joint between the pushwire and the coil. The coil can then serve to mechanically occlude a significant volume of the aneurysm and thereby reduce blood circulation within the aneurysm. After a period of time ranging from several hours to several weeks, the volume of the aneurysm can become fully occluded as blood clots about the coil. Eventually, the aneurysm will be reduced and reabsorbed by the body's natural wound healing process. This type of vaso-occlusion system was disclosed by Gugliemli in U.S. Pat. Nos. 5,122,136 and 5,354,295.

Another manner of treating an aneurysm was disclosed by Gugliemli (see U.S. Pat. Nos. 5,976,131; 5,851,206) and is described as electrothrombosis. In this particular approach, a catheter and pushwire are used to push a wire coil into the aneurysm that is connected to an electrical source. The system then delivers radiofrequency (Rf) current to the coil which is adapted to heat the blood volume within the aneurysm to cause thermal formation of thrombus (see U.S. Pat. No. 5,851,206; Col. 5, line 5). The conductive coil disclosed by Guglielmi in U.S. Pat. No. 5,976,131 has an insulated tip or other arrangements of insulation around the coil to prevent localized "hot spots" (see U.S. Pat. No. 5,976,131; Col. 3, line 53).

It is believed that several risk factors are involved in any uncontrolled use of significant levels of Rf energy to cause so-called electrothrombosis. Most important, the use of electrical energy to cause current flow between a coil (first electrode) within an aneurysm and a ground (a second body electrode) will likely cause high energy densities and highly localized heating of tissue that comes into contact with the coil. If the wall of the aneurysm contacts the energized portion of a coil, there is a significant danger of perforation or ablation of the aneurysm wall that could be life-threatening. Further, the use of uncontrolled energy delivery to an implanted coil could heat adjacent brain tissue to excessive levels resulting in loss of brain function or even death. For these reasons, the coils disclosed by Gugliemli were provided with an insulating material covering the tip of the coil that is most likely to come into contact the wall of the aneurysm. However, it is still likely that unwanted localized heating will occur within the aneurysm sac when attempting to cause ohmic heating of the blood volume in an aneurysm by creating Rf current flow between an electrode coil and a body electrode.

Another disadvantage of using the typical commercially available wire coil is that the physician must estimate dimensions and volume of the aneurysm and then feed multiple coils into the aneurysm. The deployment of each coil is time consuming, and the detachment of the coil from the introducer pushwire also is time consuming.

SUMMARY OF THE INVENTION

In general, this invention comprises a vascular occlusion system for treating aneurysms that provides a novel class of continuous extruded polymer embolic elements that carry thin metallic or conductive coatings that provide a specified resistivity to electrical current flow. Alternatively, the polymer element is fabricated with such specified resistivity by providing conductive microfilaments or conductive particles embedded within an extruded polymer element. The embolic element is introduced into a targeted site in a patient's vasculature by a microcatheter sleeve. The thin metallic coating allows the embolic element to be soft and flexible, and more importantly, allows the physician to select any desired length (and volume) of embolic element in vivo for causing mechanical occlusion of the aneurysm. The system of the invention also provides an electrical source and computer controller for feedback modulation of power delivery with a first (low) range and a second (high) range to accomplish two different methods of the invention. The electrical source is coupled to an electrode arrangement at the distal terminus of the catheter sleeve that contacts the surface of the embolic element as it is slidably deployed from the catheter. Thus, energy is delivered to the resistive layer of the embolic element directly from the distal terminus of the catheter sleeve. The catheter working end also carries a thermocouple, coupled to feedback circuitry, for sensing the temperature of the deployed embolic element and controlling its temperature via power modulation. The embolic element can be fabricated with a resistive metallic component to cooperate with single electrode have a single polarity at the catheter working end. Alternatively, the embolic element can be fabricated with spaced apart metallic surface portions to cooperate with bi-polar electrodes at the catheter working end.

In a method of using an exemplary system, the physician pushes the embolic element from the distal terminus of a catheter into a targeted site in a patient's vasculature thereby mechanically occluding a selected volume of the aneurysm or other vascular malformation. After disposing a selected length of the embolic element within the targeted site, the physician then actuates the electrical source via the controller to deliver electrical current within a first (low) power range to the conductive component of the polymer element from the electrode at the catheter's distal terminus. The electrical energy delivery to the metallic component that provides the specified resistivity (e.g., preferably ranging between about 0.5 ohms and 25 ohms/cm. of embolic element) causes resistive heating of the surface of the deployed embolic element over a particular calculated length of the element that extends distally from the electrode. This thermal effect causes denaturation of blood components that results in the formation of layer of coagulum about the deployed embolic element. Additionally, the current flow within this first range causes active or ohmic heating of blood proximate to the embolic element in a manner that facilitates the formation of the coagulative layer about the embolic element. During energy delivery, the temperature sensor at the catheter working end sends signals to the controller that are used to modulate power delivery to maintain the embolic element at, or within, a particular temperature or range at the catheter's distal terminus. By this manner of operation, the system can controllably create a selected thickness of coagulum about the surface of the embolic element. Thus, the initial deployment of the selected length of the embolic element mechanically occludes or occupies a selected (first) volume of a vascular malformation. Thereafter, controlled energy delivery thermally induces a layer of coagulative to form, thereby providing another selected volume of material to occlude or occupy a selected (second) volume of the vascular malformation. These methods of the invention provide means to cause rapid mechanical occlusion of blood flow within the malformation while preventing any significant energy densities in the targeted site.

In the next manner of practicing a method of the invention, the physician directs the controller and electrical source to deliver current at a second (higher) power level to the metallic component of the embolic element from the same electrode arrangement at the catheter's distal end. This second power level causes the metallic component together with the polymer core of the embolic element to act like a fuse at the catheter sleeve's terminus. This selected power level, within a fraction of a second, can thermally melt or divide the deployed portion of the continuous polymer embolic element from the remainder of the element still within the catheter sleeve. This aspect of the method of the invention allows the physician to select any length of embolic element intra-operatively under fluoroscopy, which is not possible in the prior art.

The invention advantageously provides a system and method for intra-operatively disposing any selected length and selected volume of an occlusive element in a targeted site in a patient's vasculature to mechanically occlude a malformation.

The invention provides a system and method that does not require the physician to pre-select a particular length of a coil element for implantation in an aneurysm.

The invention provides a system and method that does not require the physician to deploy multiple separate coil elements in separate sub-procedures to occlude an aneurysm.

The invention advantageously provides a system and method that utilizes a polymer embolic member that carries a metallic component with a specified resistivity to current flow to thereby allow controlled energy delivery within, and about, the member to create a pre-determined thickness of coagulum about the embolic member for mechanically occluding a vascular malformation.

The invention provides a system with feedback control that modulates power delivery from a source to an embolic element to maintain the embolic element at a specified temperature or within a specified temperature range.

The invention provides a system with feedback control that modulates power delivery to create a pre-selected thickness and volume of occlusive material about an embolic element.

The invention provides a self-terminating electrical energy delivery modality for creating a layer of occlusive material about an embolic element.

The invention advantageously provides a system and method that allows the delivery of electrical energy to an embolic element within an aneurysm without the risk of localized high energy densities.

The invention advantageously provides a system and method that delivers electrical energy to an embolic element to increase the volume of occlusive material in an aneurysm while eliminating the risk of perforating the wall of the aneurysm.

The invention provides a system and method that delivers electrical energy to an embolic element to increase the volume of occlusive material in a cerebral aneurysm while preventing collateral thermal damage to brain structure.

The invention provides an embolic member with a specified resistivity by fabricating the a polymer member with at least one very thin conductive surface layer.

The invention provides an embolic member with a specified resistivity by fabricating the polymer extrusion with conductive microfilaments embedded therein.

The invention provides an embolic member with a specified resistivity by extruding a polymer matrix with conductive particles embedded therein.

The invention advantageously provides a system and method utilizes a polymeric element with first and second portions of a metallic cladding that is adapted to serve as a bi-polar electrode arrangement for creating a coagulative layer.

The invention provides a method for controllably creating a coagulative volume about an embolic member by (i) controlling the center-to-center distance between spaced apart conductive components of the embolic member, and (ii) controlling the rate of energy delivery between the spaced apart conductive portions.

BRIEF DESCRIPTION OF THE DRAWINGS

Other objects and advantages of the present invention will be understood by reference to the following detailed description of the invention when considered in combination with the accompanying Figures, in which like reference numerals are used to identify like components throughout this disclosure.

FIGS. 14A-14C are illustrations of the method of practicing the invention, wherein:

FIG. 14A depicts the mesh-like polymer sleeve carries in a non-expanded position at the working end of a catheter;

FIG. 14B depicts expansion of the mesh-like polymer sleeve by expansion means comprising at least one balloon; and FIG. 14C depicts the mesh-like polymer sleeve fused to the vessel wall across the vascular malformation after delivery of electrical energy to the filaments.

DETAILED DESCRIPTION OF THE INVENTION

Figure 1:
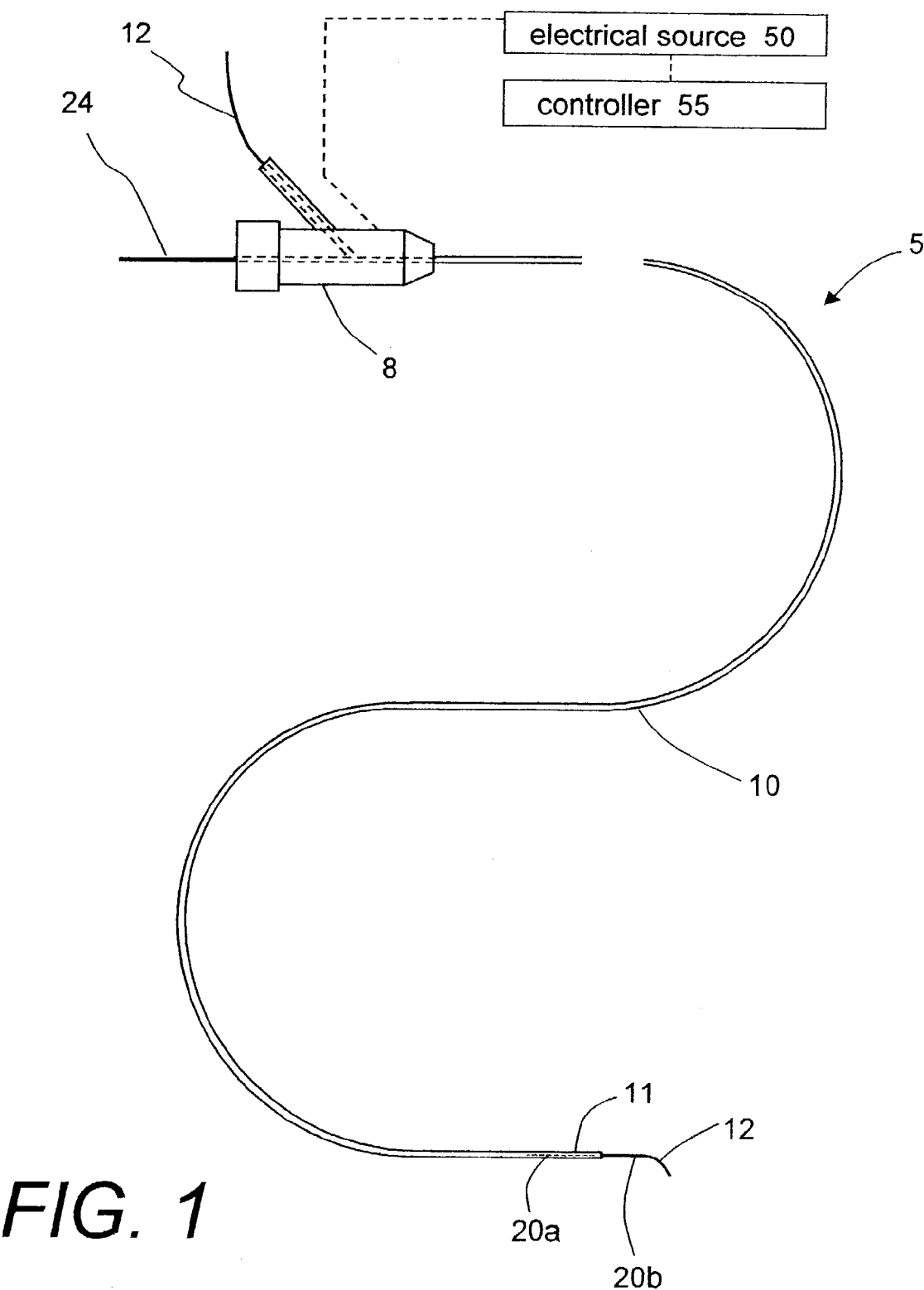
FIG. 1 shows a plan view of Type "A" vaso-occlusive system with an elongate catheter sleeve that carries the polymer embolic element made in accordance with the principles of the present invention.
Figure 2:
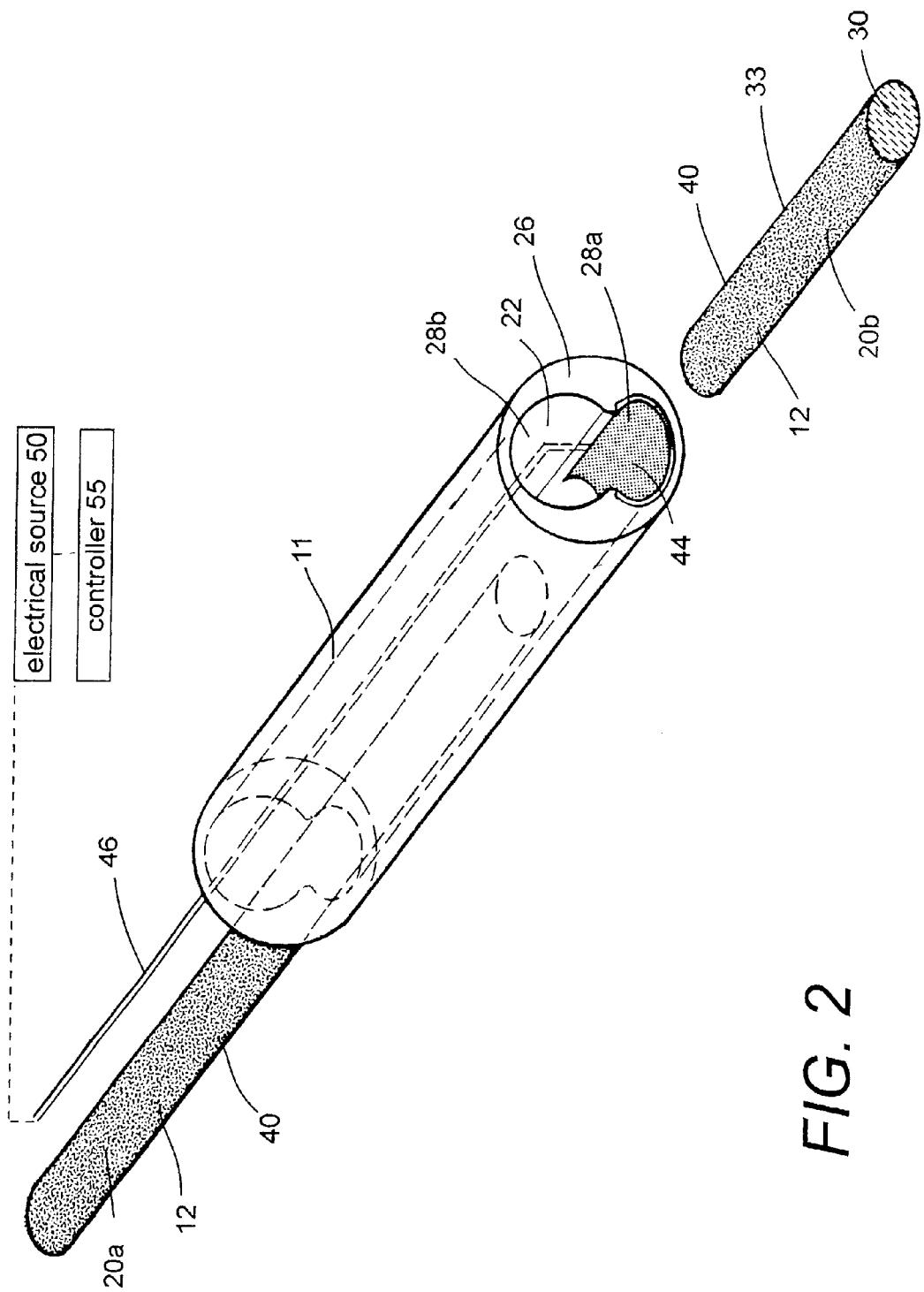
FIG. 2 is an enlarged cut-away view of the working end of the catheter sleeve of FIG. 1 showing an exemplary polymer embolic element with a metallic coating and an electrode arrangement carried within the catheter sleeve.

1. Type "A" embodiment of vascular occlusive system. FIG. 1 shows an elevational view of a Type "A" catheter system 5 for occluding an aneurysm or other vascular malformation. The catheter system has a proximal handle or manifold 8 as is known in the art that is coupled to an elongate microcatheter sleeve 10. FIG. 2 is a cut-away view of the working end 11 of catheter sleeve 10 that illustrates the metallic-coated elongate thread or filament element 12 corresponding to present invention that can be passed axially through the cooperating microcatheter sleeve 10. The flexible embolic element 12 defines a proximal portion 20a still carried within catheter sleeve 10 and a distal thread portion 20b that is pushed outward of the catheter. In this exemplary embodiment, the embolic element 12 has an oval or flattened cross-section, but other cross-sectional shapes are suitable.

Figure 3:
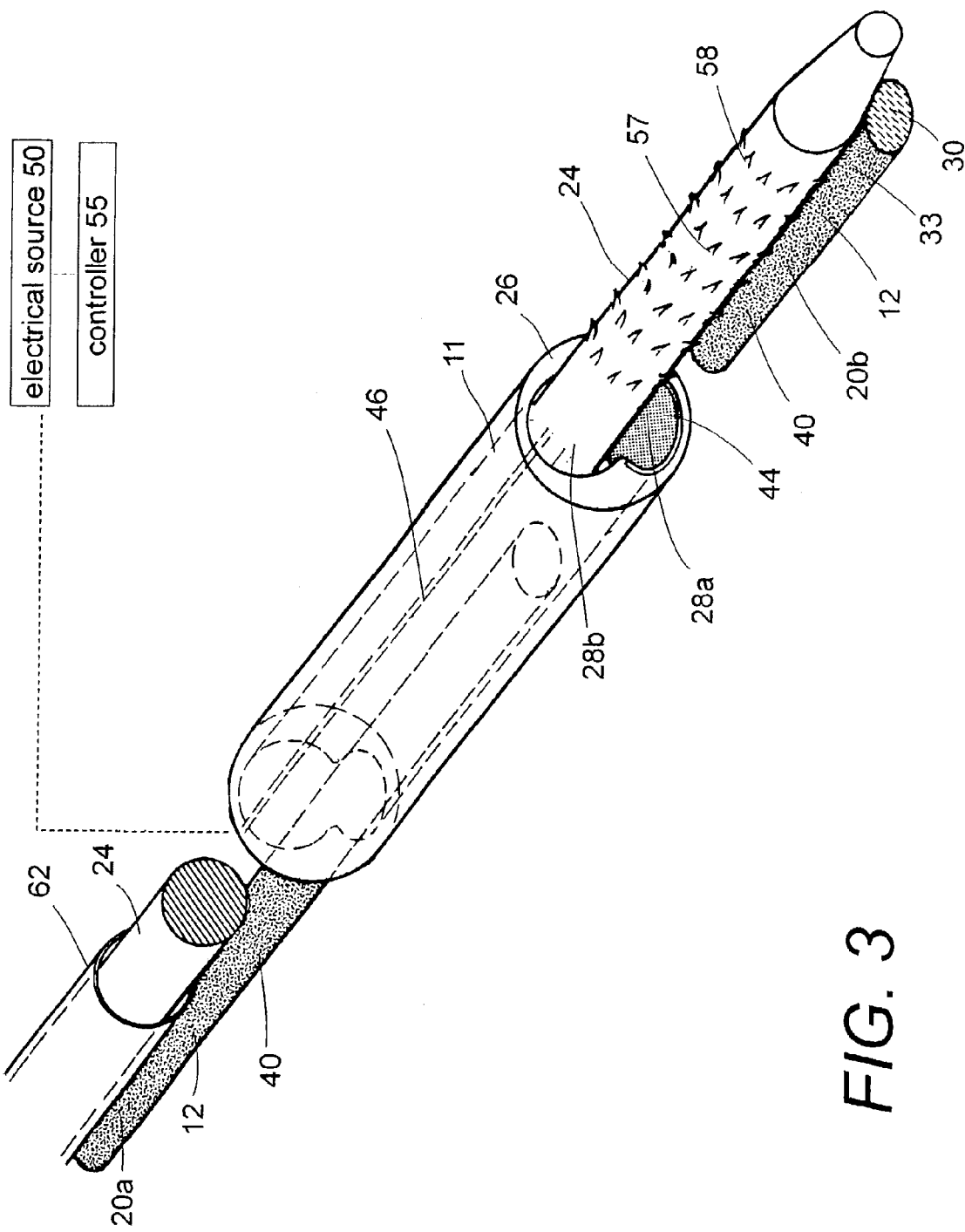
FIG. 3 is a cut-away view of the working end of FIG. 2 with an exemplary extension member adapted for pushing the polymer embolic element member distally from the catheter sleeve.
Figure 4:
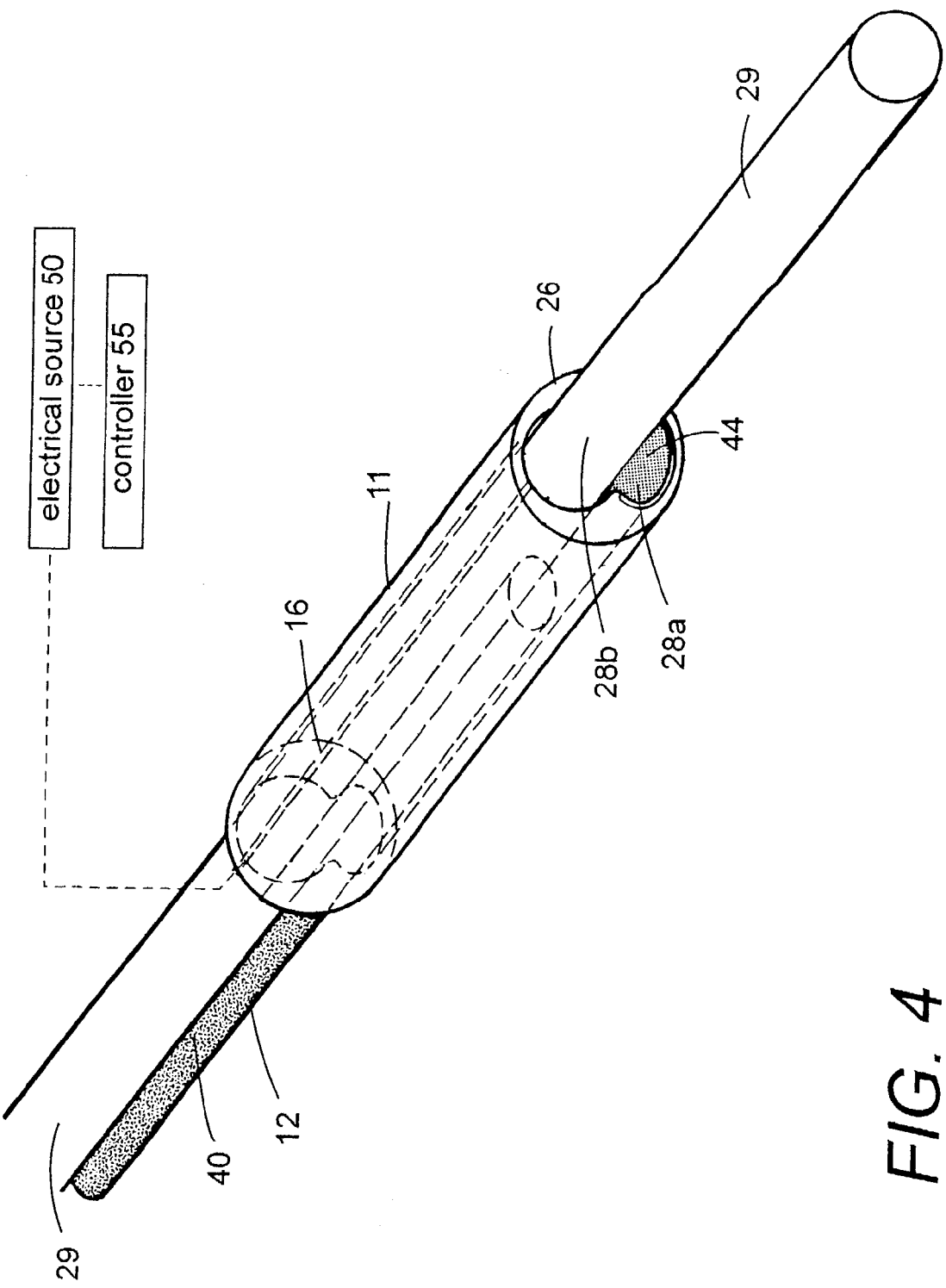
FIG. 4 shows the manner in which the working end of FIG. 2 can be introduced over a guidewire.
Figure 5A:
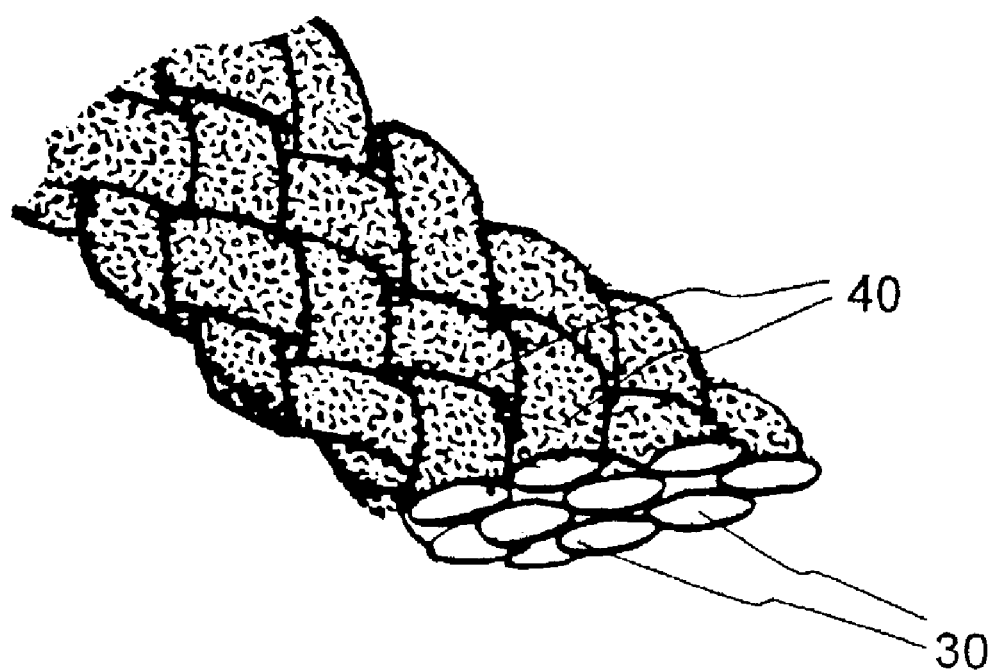
FIG. 5A is view of view of a portion of an alternative embolic element made up of multiple metallic coated filaments.
Figure 5B:
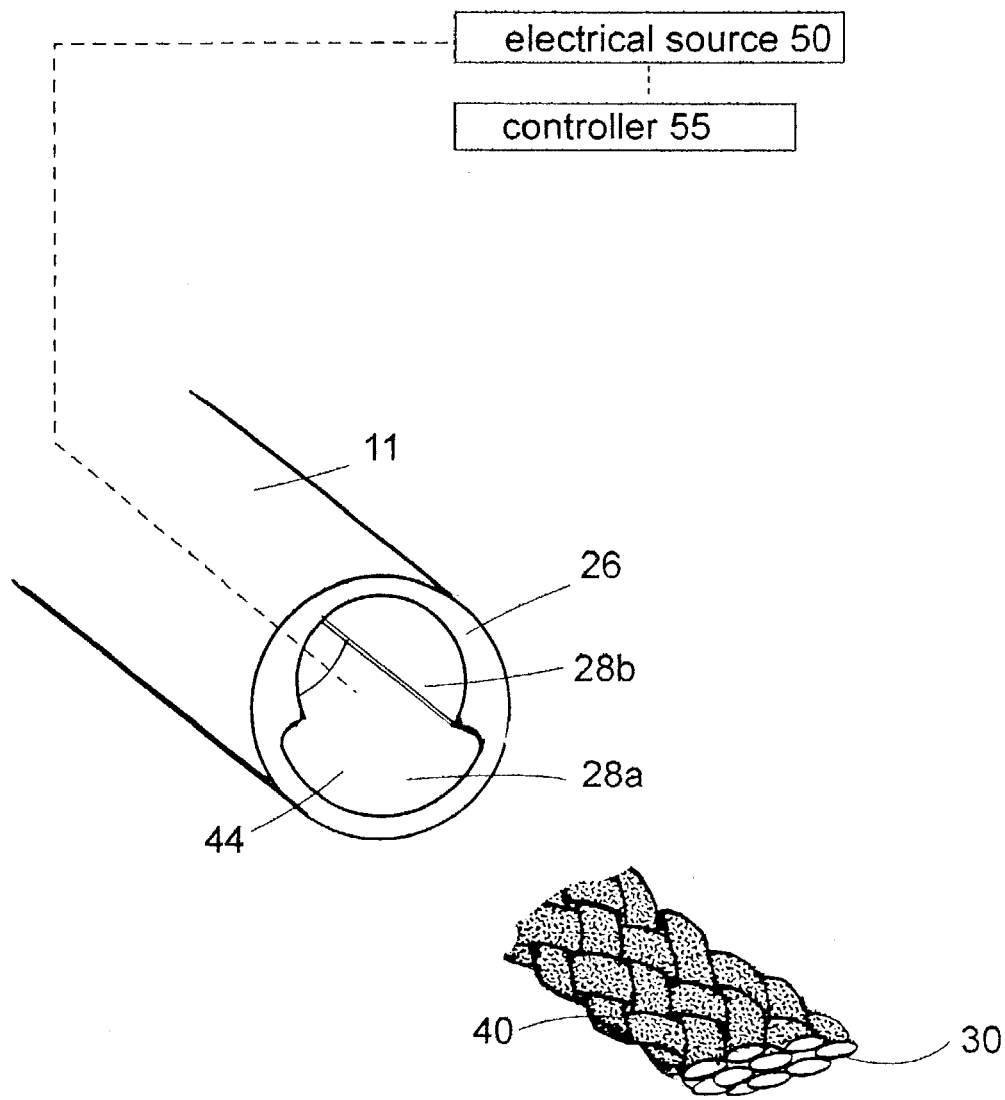
FIG. 5B is a view of the passageway in an alternative embodiment of catheter sleeve that cooperates with embolic element of FIG. 5A.

In this exemplary embodiment, an internal bore or passageway 22 within the catheter sleeve 10 is adapted to carry the embolic thread element 12 as well as to receive a slidable extension member 24 for pushing the polymer thread element 12 from the distal termination 26 of the catheter (see FIG. 3). As can be seen in FIGS. 2 & 3, the cross-sectional form of passageway 22 in the catheter sleeve has a first oval-shape bore portion indicated at 28a for carrying the polymer thread element 12 and a second round-shape bore portion indicated at 28b for slidably receiving the round extension member 24. The second bore portion 28b also is adapted for sliding over a guidewire 29 as shown in FIG. 4. It should be appreciated that the embolic element 12 and cooperating passageway 22 in the catheter sleeve 10 can be formed in several cross-sectional shapes and configurations (e.g., round, flattened and flexible, braided, etc.) and is shown in FIGS. 5A-5B with the embolic element comprising a flattened braid of polymer microfilaments. The cooperating extension member 24 may have and suitable type of mechanism for pushing, pulling, helically advancing, or otherwise expelling the embolic element 12 from distal termination 26 of the catheter sleeve.

Referring now to FIGS. 1 & 2, it is possible to describe several features and characteristics of embolic thread element 12 that adapt it for use in occluding an aneurysm sac or any other vascular malformation. The embolic element 12 has a core 30 of a continuous length of a flexible biocompatible polymeric material, such as nylon, PET, polyamide, aramid fiber, urethane or Kevlar®. The total length of the embolic element or member 12 may range from about 40 cm. to 2000 cm. The cross-sectional dimension of embolic element 12 may range from about 0.0005" to 0.030" in a round cross-section element, or similar cross-sectional area in any rectangular or other sectional shape. A suitable polymer material can be fabricated in an extrusion process, for example, by Polymicro Technologies LLC, 18019 N. 25th Ave., Phoenix, Ariz. 85023-1200. The polymer embolic element 12 further carries a radio-opaque composition as in known in the art (e.g., $BaSO_4$, $BiO_3$) to allow fluoroscopic viewing of embolic element 12 as it is maneuvered within a patient's vasculature. The core 30 of the embolic element 12 preferably (but optionally) is somewhat porous thus resulting in an irregular surface indicated at 33 to improve the gripping surface of thin-layer conductive or metallic coating 40 on the embolic element as is described next. FIGS. 5A-5B show an embolic element 12 comprising a plurality of small diameter filaments 42 woven into a flexible braid, with each filament having a metallic coating as described below. A braided embolic element 12 such as depicted in FIG. 5A also would provide a suitable surface 33 for gripping with extension member 24 as described below. It should be appreciated that the flexible embolic element may have a curved or coiled repose shape, and then be straightened as it is passed through the catheter sleeve. Upon deployment, the embolic element would again assume its repose coiled shape to facilitate its introduction into an aneurysm.

As can be seen in FIG. 2, the embolic element 12 carries a thin-layer conductive or metallic coating 40 that has a selected electrical resistivity for accomplishing a method of the invention described below. The metallic coating 40 may be any suitable biocompatible material that can be formed in, or deposited on, the elongate polymeric element 12, such as gold, platinum, silver, palladium, tin, titanium, tantalum, copper or combinations or alloys of such metals, or varied layers of such materials. A preferred manner of depositing a metallic coating 40 on the polymer element comprises an electroless plating process known in the art, such as provided by Micro Plating, Inc., 8110 Hawthorne Dr., Erie, Pa. 16509-4654. The preferred thickness of the metallic coating ranges between about 0.00001" to 0.005". More preferably, the coating thickness ranges between about 0.0001" to 0.001". Still more preferably, the thickness of the conductive coating ranges between about 0.0005" to 0.0007". As will be described below in the Type "C" embodiment, the polymer element also may be extruded with conductive filaments or particles embedded within the polymer matrix of core 30 of the element.

Of particular interest, the combination of the core 30 and metallic or conductive coating 40 of the embolic element 12 provides a selected resistivity to current flow that ranges from about 1 ohm to 500 ohms per 10 cm. length of the embolic element 12 to cause controllable heating about the surface 33 of embolic element 12. More preferably, the element provides a resistivity ranging between about 5 ohms to 250 ohms per 10 cm. length. Still more preferably, the core 30 and conductive coating 40 provide a selected resistivity ranging between about 30 ohms to 60 ohms per 10 cm. length of the embolic element 12.

FIGS. 2 & 3 further illustrate that the distal end of catheter sleeve 10 carries a conductive electrode surface indicated at 44 about a distal region of bore portion 28a that carries embolic element 12. The electrode 44 is coupled to electrical lead 46 that extends within the wall 48 of the catheter to its proximal handle end and to electrical source 50 and controller 55. It should be appreciated that the electrical lead 46 can be a part of a helical braid reinforcement within the catheter sleeve. As can be easily understood by viewings FIGS. 2 & 3, the elongate embolic element 12 can be pushed distally from bore portion 28a, and no matter the axial position of the embolic element, and electrode 44 will substantially contact the metallic surface 40 of the polymer element 12. As will be described below in the method of the invention, the electrical source 50 and electrode arrangement of catheter 10 in combination with the metallic coating of the polymer element 12 are adapted to (i) facilitate rapid occlusion of an aneurysm, and (ii) to sever or divide the polymer thread element 12 to thereby implant any selected length of distal portion 20b of polymer element 12 within in the aneurysm while retaining a proximal length 20a of the polymer element in bore 28a of the catheter. As shown in FIG. 3, the electrode 44 is shown for convenience at the distal end of the catheter sleeve. Preferably, the electrode 44 is spaced slightly inward or proximal from the distal termination 26 of the sleeve to prevent any substantial electrode surface from being exposed to the blood volume proximate to a targeted treatment site.

Figure 5C:
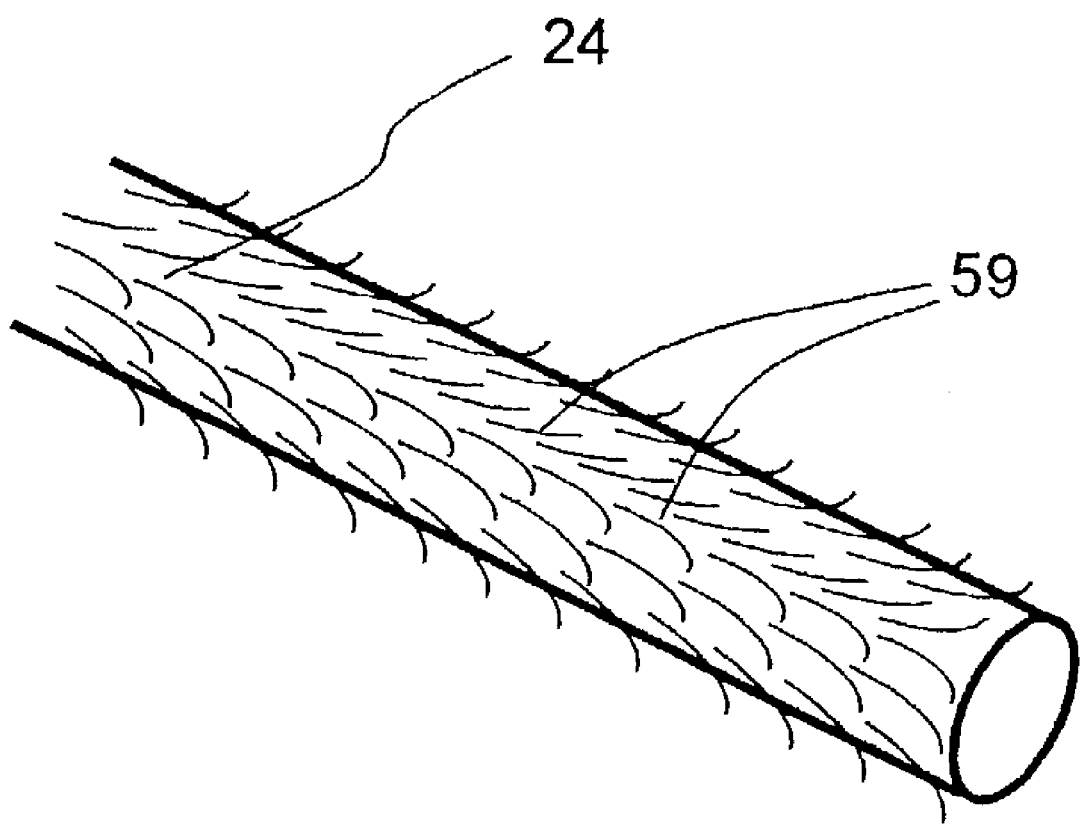
FIG. 5C is a perspective view of an alternative embodiment of extension member adapted to grip the embolic element.

In the system shown in FIGS. 2 & 3, the exemplary polymer element 12 is very soft and flexible, for example, having the flexibility characteristics of a common thread or suture. In order to deploy the polymer thread element 12 from distal termination 26 of catheter sleeve 10, this embodiment utilizes a slidable extension member 24 that has unidirectional gripping elements 57 (herein alternatively called barbs) about a distal region 58 of the extension member 24. As can be understood in viewing FIG. 2, an axial movement or projection of extension member 24 from sleeve 10 will cause the barb elements 57 to grip the embolic element and pull it from bore portion 28a. When the extension member 24 is moved proximally in bore portion 28b, the barb elements will slide over surface 33 of embolic element 12 thus leaving a selected length of the embolic element disposed outside distal termination 26 of the catheter sleeve. The barb or gripping elements 57 may be provided in extension member 24 may comprise cuts into the surface of a polymer extension member 24. Alternatively, the gripping elements may comprise a fiber or other type of hair-like filament 59 bonded to the surface of an extension member 24 as shown in FIG. 5C.

The catheter sleeve 10 while carrying the polymer embolic element in bore portion 28a may be introduced into vasculature over a guidewire 29 as shown in FIG. 4. The guidewire then can be removed and be replaced by the extension member 24. To facilitate the slidable introduction of the extension member 24 and grip elements into bore portion 28b while embolic element 12 is carried within bore portion 28a, the extension member may cooperate with a very thin-wall sleeve 62 of Teflon® or any other suitable material to prevent the gripping elements 57 from gripping the embolic element 12 as the guidewire is replaced with the extension member 24. As can easily understood from viewing FIG. 3, to expose the distal portion 58 of the extension member 24 and gripping elements 57, the thin-wall sleeve 62 can be retracted from the gripping elements by pulling it proximally at the handle 8 of the catheter.

The system 5 further provides feedback control mechanisms within controller 55 for modulating energy delivery to electrode 44 and thereby to the conductive component of the embolic element. Referring again to FIG. 3, at least one thermocouple 88 is provided at either surface of electrode 44 to measure the temperature of the electrode which is substantially the same as the surface temperature of the embolic element in contact therewith. The thermocouple 88 is linked to controller 55 by an electrical lead (not shown). The controller 55 is provided with software and algorithms that are adapted to modulate power delivery from electrical source 50 to maintain the temperature of the embolic element (or electrode 44) at a particular level or within a particular temperature range, in response to feedback from the sensor.

Figure 6A:
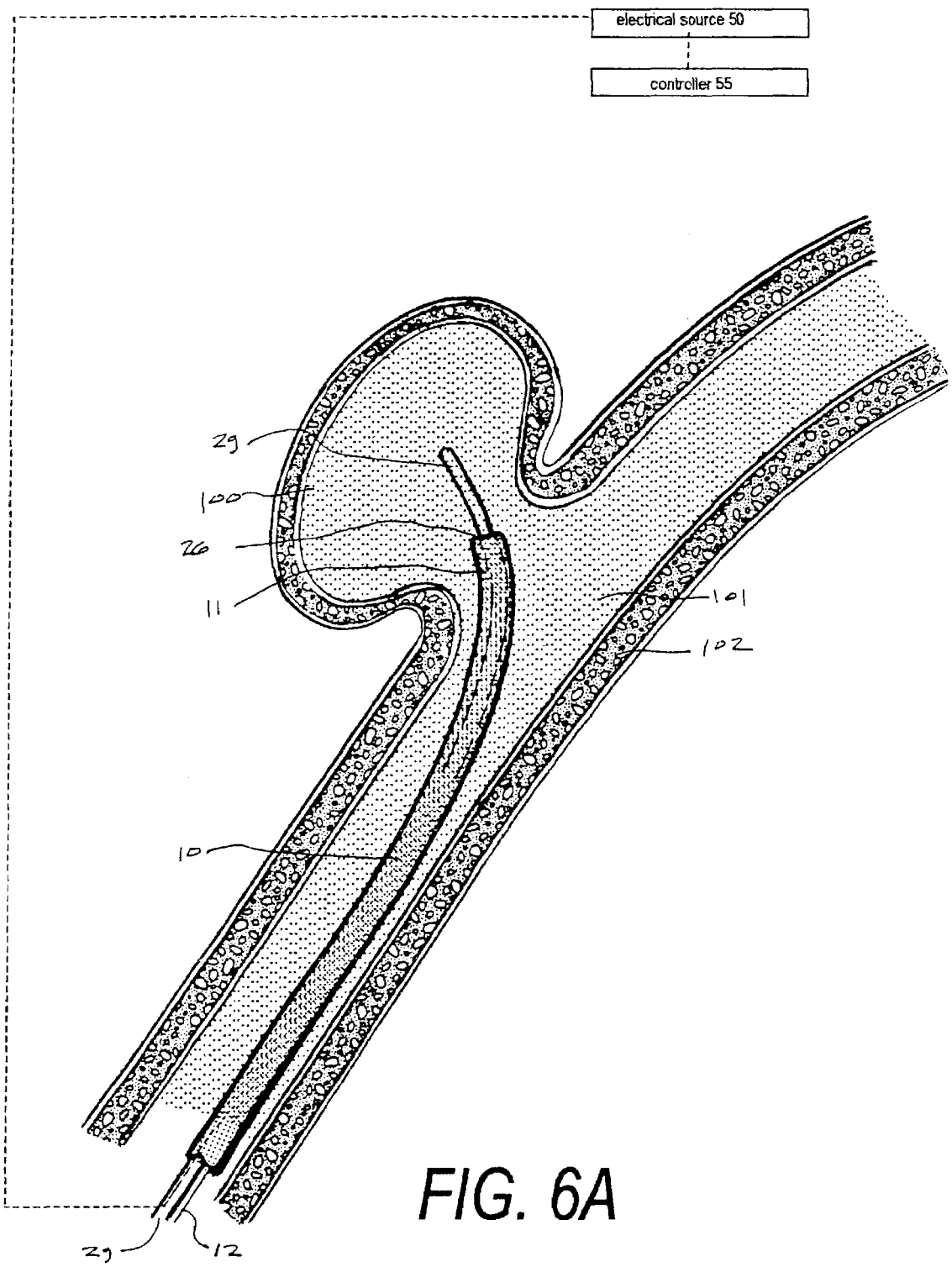
FIG. 6A is a view of the working end of the Type "A" system of FIGS. 1 & 2 disposed in a blood vessel proximate to an aneurysm.
Figure 6B:
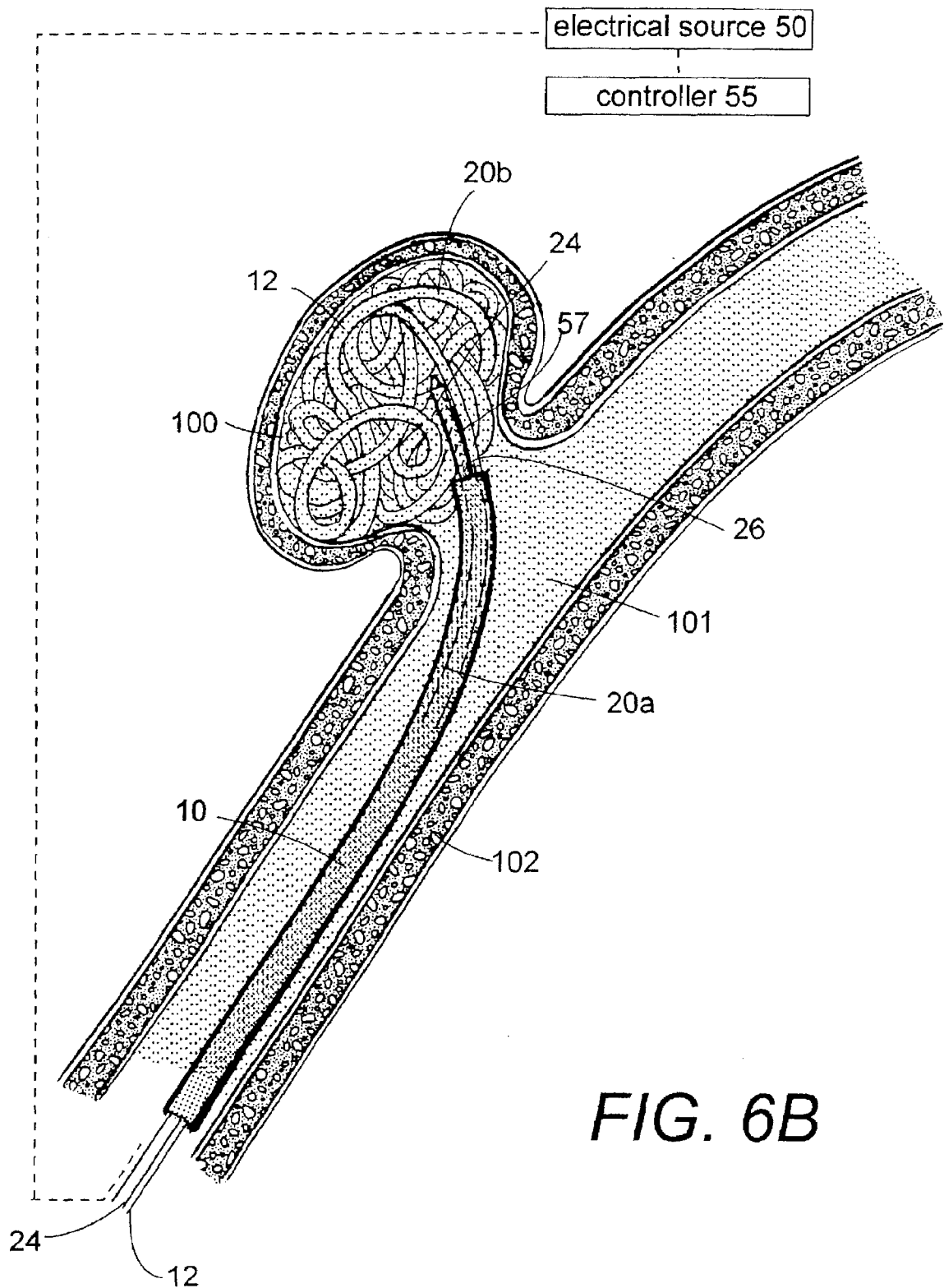
FIG. 6B is a view of the working end of FIG. 6A after a selected length of a distal portion of the polymeric member is disposed in the aneurysm and formed into a tangled mass to occupy a volume of the aneurysm.

Now turning to FIGS. 6A-6B, the manner of using the catheter system 5 to introduce the polymer embolic element 12 into a cerebral aneurysm indicated at 100 or any other targeted vascular site is shown. In FIG. 6A, it can be seen that working end 11 of catheter sleeve 10 is introduced through blood 101 flowing in vessel 102 until its distal termination 26 is positioned adjacent to, or partially within, the aneurysm 100. Typically, the catheter is guided to the aneurysm over guidewire 29 that is accommodated by bore portion 28b of the catheter sleeve (see FIGS. 4 & 6A). In FIG. 6B, it can be seen that guidewire 29 has been withdrawn from catheter passageway 28b, and thereafter the extension member 24 has been introduced back through the same passageway. The (optional) thin-wall sleeve 62 as shown in FIG. 3 is withdrawn to expose gripping elements 57 at distal portion 58 of the extension member. FIG. 6B depicts an elongate distal portion 20b of the embolic element 12 being disposed in the aneurysm sac 100 which has been caused by pushing the extension member 24 to and fro thereby causing the grip elements 57 to engage surface 33 of embolic element 12 and successively carry small axial lengths of element 12 distally into the aneurysm under fluoroscopic control. In this manner, any selected length of distal portion 20*b* of polymer element 12, for example from about 5 cm. to 200 cm. for a typical aneurysm, can be fed into the malformation. The selected length and volume of embolic element 12 thereby displaces blood 101 and occupies a selected (first) volume of the vascular malformation.

As can be seen in FIG. 6B, the volume of aneurysm 100 can be substantially occupied with the embolic element 12, depending on its flexibility, to accomplish a first aspect of the method of the invention. In effect, the embolic element 12 causes an initial partial mechanical occlusion of the aneurysm volume by implanting a selected volume of occlusive material (ie., the entangled length of polymer element 12) within the aneurysm which displaces a similar volume of blood 101 and thereby slows blood flow through the aneurysm and pressure therein. Next, a second novel aspect of the method of the invention is practiced wherein electrical energy is controllably delivered to embolic element 12 to increase the volume of occlusive material within the aneurysm by adding a layer of coagulum 104 about the polymer embolic element 12 thereby occupying a second volume of the aneurysm.

Figure 6C:
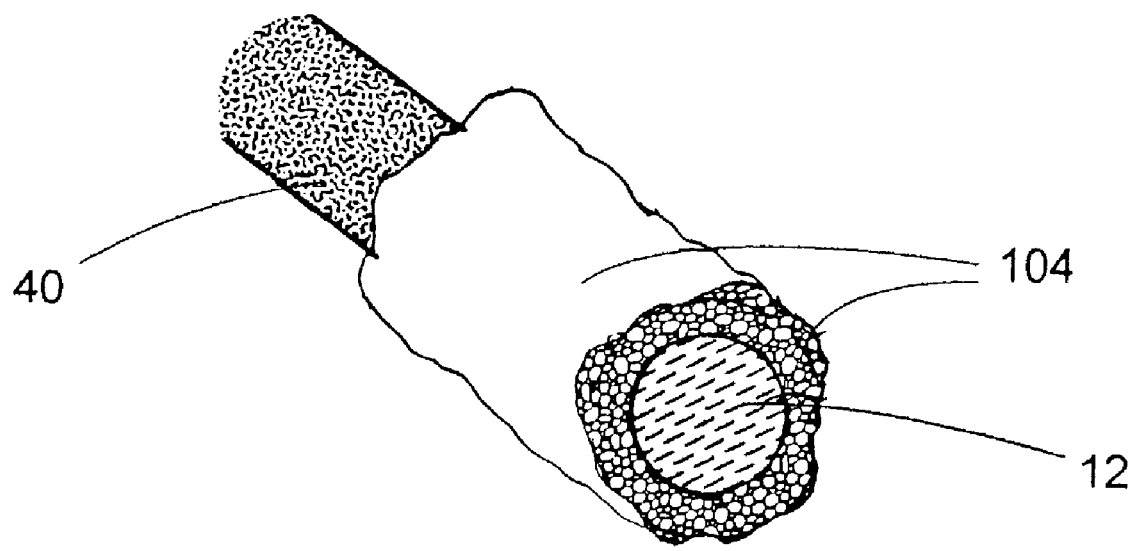
FIG. 6C is a graphic view of portion of a polymer embolic element with coagulum formed around the element by resistive heating of the metallic surface to increase the volume of occlusive material within a malformation.

More in particular, referring to FIGS. 6B & 6C, after the selected length of distal portion 20*b* of polymer element 12 is fed into aneurysm 100 under fluoroscopic control, the physician actuates the electrical source 50 via controller 55 to deliver electrical energy to electrode 44. The contact between electrode 44 and metallic surface 40 of polymer element 12 causes current flow along the metallic surface 40 of the entangled element and within the patient's body to a return electrode such as a ground pad in contact with the patient's body. The selected resistivity designed into the combination of metallic coating 40 and embolic element core 30, as described above, causes resistive heating of the element 12. The temperature of the surface 33 of the embolic element (as well as slight active ohmic heating of blood about the element 12) causes denatured blood products and coagulum to adhere about surface 33 of the embolic element. As depicted graphically in FIG. 6C, the thermally-induced coagulation of blood 101 causes a substantial layer of coagulum 104 to form around the embolic element 12 to thus provide a greater volume of occlusive material within the aneurysm 100. In a preferred mode of operation, the thermocouple 33 (see FIG. 3) together with feedback circuitry to the controller 55 are used to modulate power delivery to electrode 44 to maintain the embolic element at the catheter terminus at a pre-selected temperature level for a selected period of time. The method of invention maintains the surface temperature of embolic element 12 within a range of about 45° C. to 100° C. More preferably, the surface temperature of the embolic element is maintained within a range of about 65° C. to 90° C. to create the desired coagulum. This aspect of the method of the invention thus increases the volume of occlusive material within the vascular malformation to further mechanically reduce blood circulation within the defect. Thereafter, the occlusive material (embolic element and coagulative layer) within the aneurysm then rapidly will cause accumulation of platelets and other clotting factors about the occlusive material to complete the occlusion of the aneurysm volume as a result of the body's wound healing response to the occlusive material volume within the aneurysm 100.

In accomplishing the above-described method of the invention, the electrical energy delivery provided by source 50 and controller 55 can be in the radiofrequency range and at a first power level ranging between about 1 watt and 50 watts. More preferably, the power level ranges between about 5 watts and 15 wafts. It is proposed that current flow for about 5 seconds to 1200 seconds will cause the desired thickness of coagulative material to form around the embolic element 12 to assist in the mechanical occlusion of an aneurysm or other vascular defect. It should be appreciated that the duration of power delivery is a factor in creating a desired thickness of coagulative material on the embolic element. However, the process of causing the formation of a coagulative layer about the embolic element is essentially self-terminating, which adds to the safety of practicing the method of the invention. The method is self-terminating in the sense that as the coagulative layer builds to the desired selected thickness, the layer serves as an insulative layer and thereby prevents further denaturation of blood compositions (or ohmic heating of blood proximate to the embolic element.

The method of using an embolic element having a resistivity in the selected range described above has the advantage of preventing any possibility of creating energy densities ("hot spots") within the aneurysm wall that could perforate the aneurysm sac. The low power levels utilized in this method of the invention can easily cause resistive heating of the metallic surface coating 40 for coagulation purposes, but cannot cause significant localized current flows (ie., energy densities) that could perforate a vessel wall, or create energy densities that could cause ohmic heating of collateral brain structure. Of particular importance, the thermally-induced coagulative process is effectively self-terminating since the temperature level at surface 33 of the metallic coating 40 will become insulated by the coagulum, thus preventing overheating of the interior or the aneurysm.

Figure 7:
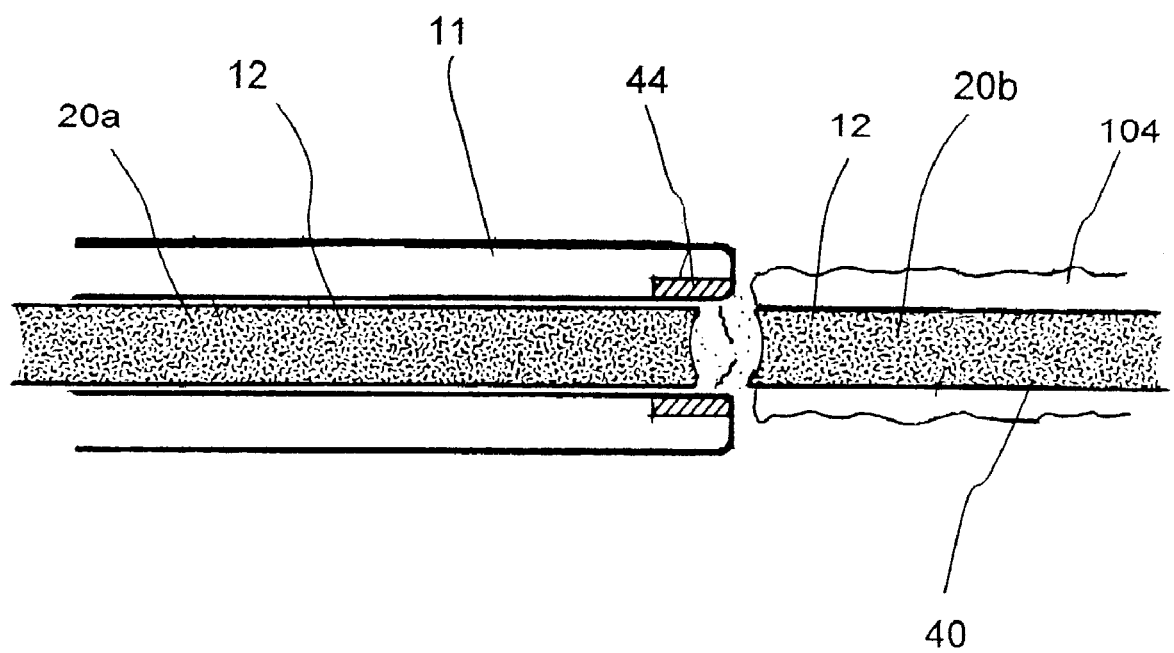
FIG. 7 is a graphic view of a manner of practicing a method of the invention in utilizing a selected level of electrical energy to divide the implanted embolic element from a proximal portion of the polymeric element still within the catheter sleeve.

FIG. 7 graphically illustrates the next step of the method of the invention that involves separation of the distal portion 20*b* of embolic element 12 entangled within aneurysm 102 (see FIG. 6B) from proximal portion 20*a* of embolic element 12 still within the catheter sleeve 10. In order to accomplish the separation of the embolic element 12 according to the invention, the physician actuates electrical source 50 via controller 55 to deliver current flow to electrode 44 that has a selected second (higher) power than the previously described power levels. As can be understood in FIG. 7, the insulative coagulum around the embolic element 12 will substantially prevent current flow at the second higher power level to course through the endovascular media, thus eliminating the possibility of high localized current densities. However, at the interface 107 between electrode 44 and metallic surface in contact with the electrode, the current flow will create a transient high energy density in and about metallic coating 40 and core 30 of element 12 to cause thermal melting of the polymer core to thereby divide the embolic element 12. To divide the embolic element, it is believed that a power level ranging between about 5 watts and 100 watts is suitable. More preferably, the power level is within the range of about 10 watts to 30 watts. It is believed that current flow for about 0.01 seconds to 20 seconds will divide the embolic element. Following the division of the implanted embolic element 12, the catheter 10 that carries the proximal portion 20*a* of the embolic element is withdrawn from the patient's vasculature.

The previously described means of dividing the embolic element with electrical energy has the particular advantage of allowing the physician to implant any desired length of the embolic element 12 within an aneurysm or other vascular defect. The physician simply can advance a length the polymer element into the defect under fluoroscopy until the entangled volume appears optimal, and then deliver electrical energy at the first and second power levels to (i) add coagulative volume to the occlusive material in the vascular defect, and then (ii) to separate the implanted embolic element 12 from the remainder of the element still within the catheter. This method of the invention, of course, can be practiced for implanting an embolic element without utilizing electrical energy to add a coagulative layer to the embolic element as described above.

In another embodiment of embolic element 12, the polymer or the metallic coating is formed in a coiled or curved shape and the material has a memory of such a curved shape. The flexible embolic element 12 then conforms to a generally linear configuration for feeding through a catheter sleeve. Upon deployment beyond the distal terminus of the catheter sleeve, the embolic element then will substantially assume its curved or coiled shape which will assist in its insertion into an aneurysm.

Figure 8:
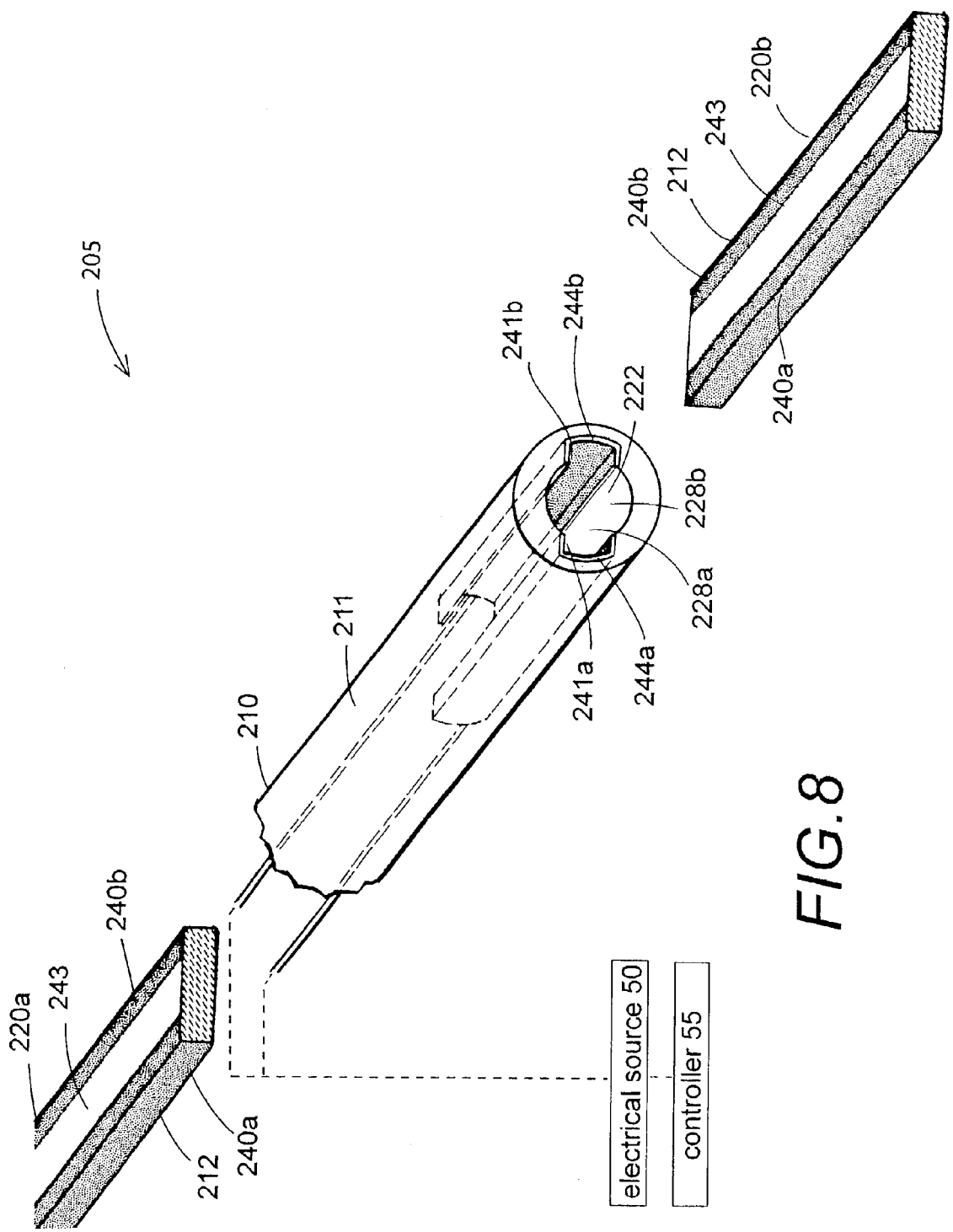
FIG. 8 is a cut-away view of the working end of Type "B" vaso-occlusive system showing a polymer embolic element with first and second spaced apart metallic coatings made in accordance with the principles of the invention.

2. Type "B" embodiment of vaso-occlusive system. FIG. 8 shows a cut-away view of a Type "B" catheter system 205 for occluding an aneurysm, other vascular defect or malformation or any targeted site within a patient's vasculature. The catheter system is similar to the previously described embodiment and has a proximal handle or manifold 8 coupled to an elongate microcatheter sleeve 210 that terminates in working end 211. As can be seen in FIG. 8, this system comprises a metallic-coated elongate member 212 that can be passed axially through the a cooperating bore 222 in the microcatheter sleeve 210. This Type "B" system differs from the previously disclosed system in that the flexible continuous embolic member 212 (that defines proximal portion 220*a* and distal thread portion 220*b*) functions in two alternative manners: (i) the flattened embolic member 212 is substantially stiffened to allow it to be pushed outward from a handle end 8 of the catheter sleeve without requiring a pushing member or extension member as described above, and (ii) the polymer embolic member 212 carries first and second spaced apart metallic coating portions to act as resistive elements and to further act as a bi-polar delivery system to perform alternative methods of the invention in creating coagulative material and in dividing the polymer embolic member 212 after implantation in a vascular malformation.

In this exemplary Type "B" system embodiment, the internal bore 222 is shaped to receive the flattened embolic thread member 212 in a rectangular shaped bore portion indicated at 228*a*. Additionally, the catheter sleeve is adapted to slide over a round guidewire (not shown) that is accommodated by the round shape bore portion 228*b*. In this embodiment, the embolic thread member 212 again has a body core 230 of a continuous length of a flexible polymeric filament. The polymer embolic member 212 again carries a radio-opaque composition.

As can be seen in FIG. 8, this alternative embodiment of embolic member 212 carries first and second opposing thin-wall metallic coating portions 240*a* and 240*b* that extend the length of the embolic member 212. The metallic coating in this embodiment again has a selected resistivity to current flow that ranges from about 1 ohm to 500 ohms per 10 cm. length, although a lesser resistivity also is functional for some methods of the invention. For example, the opposing metallic coating portions 240*a* and 240*b* can act as bi-polar electrodes as will be described below. In such an application, the first and second metallic portions 240*a* and 240*b* extends along first and second sides 241*a* and 241*b* of the entire length of the embolic member 212. It can be seen that these first and second metallic surfaces define a center-to-center dimension and can act as bi-polar electrodes, since the surface portions are spaced apart on either side of a medial non-metallic surface portion indicated at 243.

FIG. 8 further illustrates that working end 211 of catheter sleeve 210 carries spaced apart first and second conductive electrodes 244A and 244B on either side of bore portion 228*a* that carries embolic member 212. The electrodes 244A and 244B are coupled to electrical leads 246*a* and 246*b* in wall 248 that extend to electrical source 50 and controller 55. As can be understood by viewing FIG. 8, the elongate polymer member 212 is substantially stiff so that it can be pushed distally from bore portion 228*a* from the handle end of the catheter, and the electrodes 244A and 244B will always be in contact with the respective metallic surface portions 240*a* and 240*b* of the polymer element 212. Alternatively, the embolic member can be pushed distally by an extension member as described previously.

The manner of using catheter system 205 to perform the methods of occluding a cerebral aneurysm 100 can be easily described, still referring to FIG. 8. The elongate polymer member 212 is passed through the catheter sleeve 210 and thereby fed into the aneurysm 100 similar to the graphic representation of FIG. 6B. Thereafter, a guidewire (if used) is withdrawn from the catheter passageway 228*b*. Thus, the aneurysm sac can be substantially occupied with embolic member 212 to partially mechanically occlude the aneurysm volume.

Next, the physician actuates electrical source 50 via controller 55 to deliver electrical energy to common polarity electrodes 244A and 244B. The contact between electrodes 244A and 244B and the metallic surface portions 240*a* and 240*b* of embolic member 212 causes current flow along the metallic surfaces of the entangled member in cooperation with a return electrode such as a ground pad. The selected resistivity of the metallic surface portions 240*a* and 240*b* of polymer element 212 then will coagulate blood about the surface of the embolic member 212, generally as described previously to add to the volume of implanted occlusive material.

In a more preferred method of operation, the electrical source 50 and system 205 is provided with circuitry that allows controller 55 to programmably deliver bi-polar Rf current at a first power level to electrodes 244A and 244B which are in contact with the opposing metallic surface portions 240*a* and 240*b* of polymer member 212 to cause current flow between the metallic surface portions 240*a* and 240*b*. This manner of bi-polar current flow is advantageous since it will not cause high current densities in any endovascular media that might then threaten perforation of the aneurysm wall. Such bi-polar flow thus will rapidly cause a coagulative layer on the embolic member (generally between the metallic surface portions 240*a* and 240*b*) to thereby add to the volume of occlusive material within the aneurysm. In using the paired metallic surface portions 240*a* and 240*b* in such a bi-polar energy delivery modality, the metallic coatings may provide any lesser resistivity to current flow for performing the method of the invention.

In another energy delivery modality, the controller may sequence delivery of mono-polar Rf current to the working end 211 in cooperation with a ground pad and bi-polar flow between the paired metallic surface portions 240*a* and 240*b* to cause coagulum to form about the embolic member 212. The system further may use a thermocouple (not shown) and feedback circuitry as described above to maintain the surface of the embolic member within the desired temperature range as described above.

The use of the paired metallic surface portions 240a and 240b in a bi-polar mode is particularly adapted for use in the next step of the method of the invention that involves separation of the distal portion 220b of embolic member 212 entangled within aneurysm 102 (cf FIG. 6B) from proximal portion 220a still within catheter sleeve 210. In using this embodiment, the physician actuates electrical source 50 via controller 55 to deliver bi-polar Rf current flow between electrodes 244A and 244B at a selected second (higher) power level than used in the coagulation modality. In this case, the second power level causes the core 230 of embolic member 212 to resemble a fuse as the current courses between the electrodes to thus divide embolic member 212 at the distal termination 226 of the catheter sleeve. It is believed that the method of using bi-polar Rf current flow between paired electrodes will allow separation of the embolic member 212 within a range of about 0.1 to 10 seconds. Again, this embodiment of the invention then allows any suitable length of embolic member 212 to be introduced into the aneurysm—and then separated at the catheter end.

In another Type "B" embodiment, the emboli member may have a transverse section in the shape of a "C" (not shown) to partially wrap around a guidewire or a pusher member (see FIG. 3). It can be easily understood that such a cross-sectional shape would allow the "C" shape to function in the fashion of rapid-exchange catheter systems as are known in the art to insert over a guidewire. Further, this embodiment would allow bi-polar electrode surfaces on opposing and spaced apart inner and outer surfaces of the embolic member to otherwise function as described above.

Figure 9:
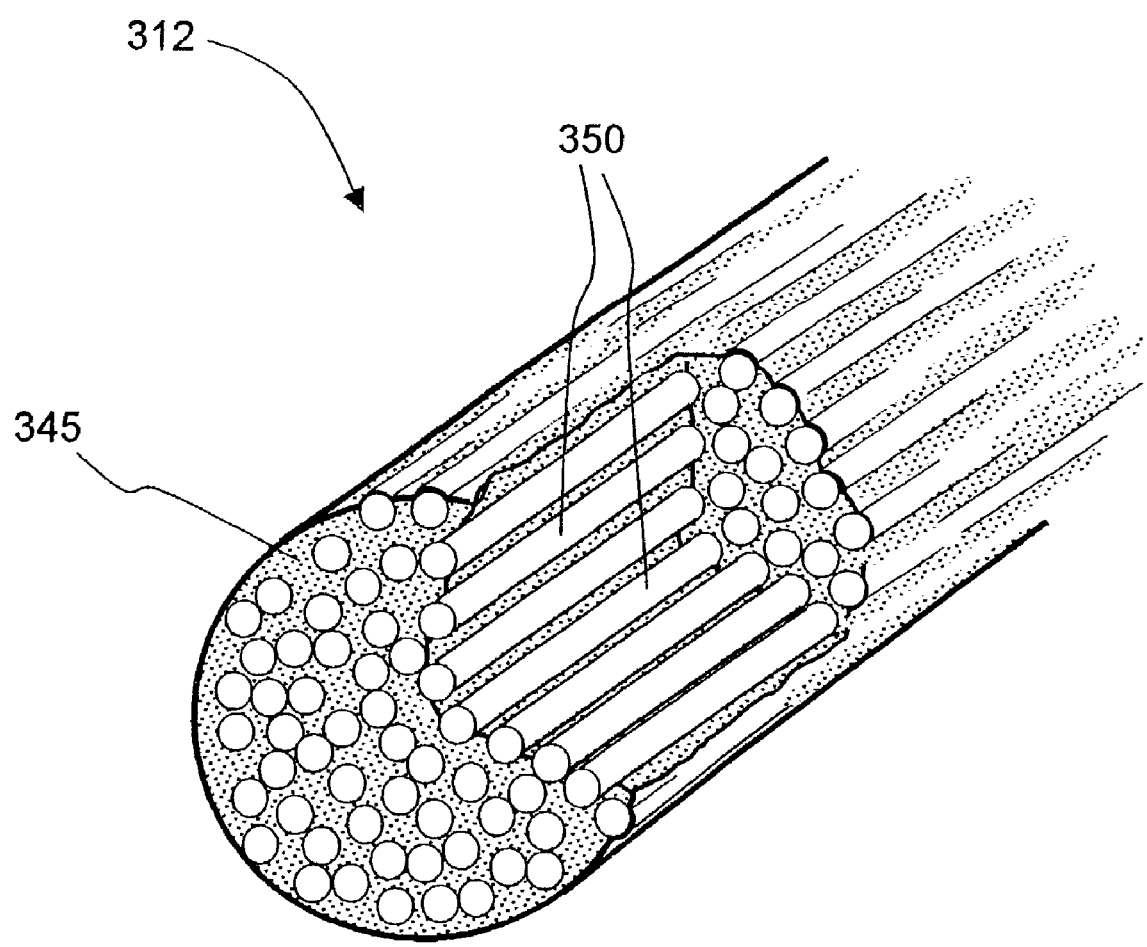
FIG. 9 is a sectional view of an embolic element of a Type "C" vaso-occlusive system wherein the embolic element comprises a matrix of a polymer with conductive microfilaments embedded therein.
Figure 10:
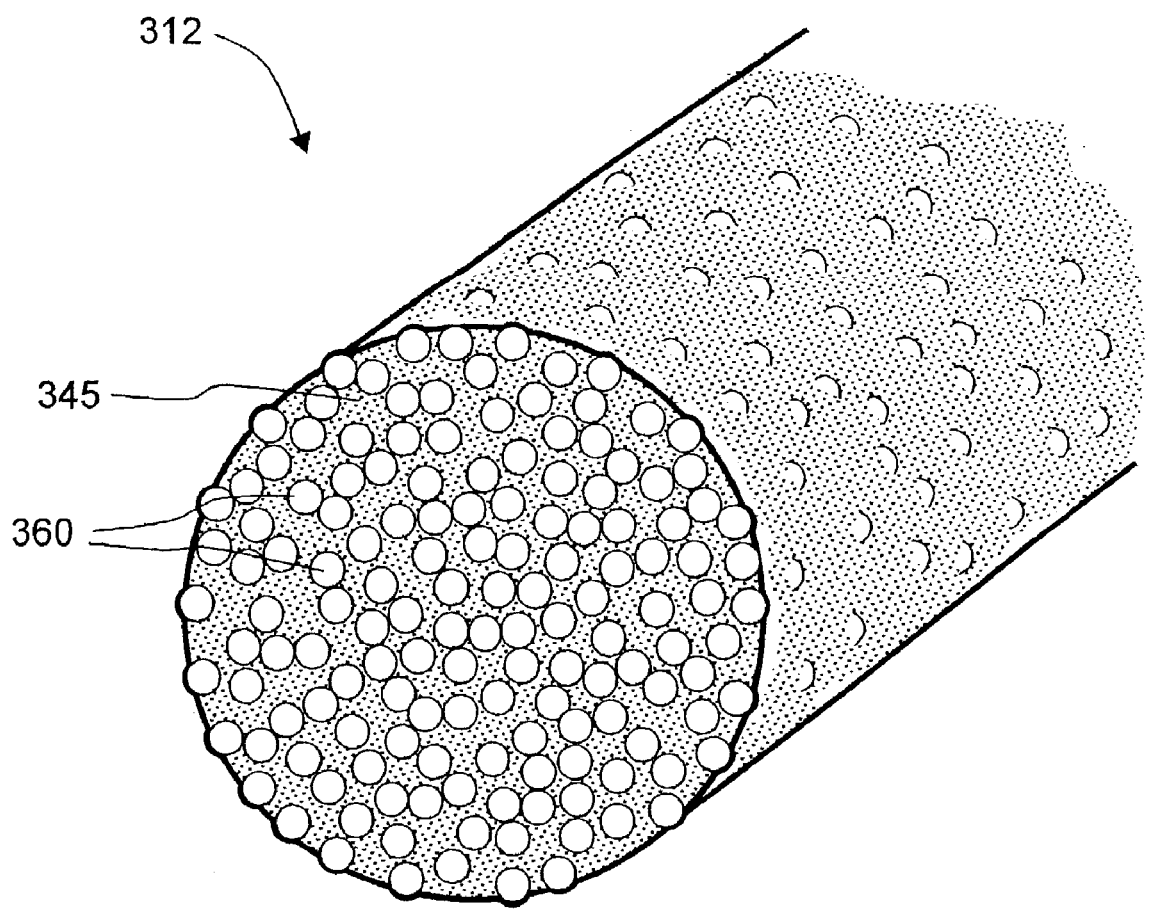
FIG. 10 is a sectional view of an alternative embolic element of a Type "C" vaso-occlusive system wherein the embolic element comprises a matrix of a polymer with conductive particles distributed therein.

3. Type "C" vaso-occlusive system. This alternative Type "C" system uses a catheter sleeve as described in the Type "A" embodiment above. This system differs only in the construction of elongate embolic member 312 shown in FIGS. 9 and 10. The flexible continuously extruded embolic member 312 again comprises a substantially polymer core together with a conductive component that provides the member with a specified resistivity. In one alternative embodiment of Type "C" embolic member shown in FIG. 9, the member 312 comprises a polymer matrix 345 that is co-extruded with micro-filaments 350 of any suitable conductive material embedded therein, such as tungsten, stainless steel or carbon fiber. The micro-filaments 350 can be partially exposed at the surface of the member to contact the electrode arrangement carried at the distal termination of the catheter sleeve. In another alternative Type "C" embolic member shown in FIG. 10, the member 312 comprises a polymer matrix 345 with embedded particles 360 of any suitable conductive material to thereby provide the resistivity specified above. The polymer conductive-resistive matrix of embolic member 312 functions as a fuse to divide the embolic member at the distal end of a catheter as described in the Type "A" embodiment.

Figure 11:
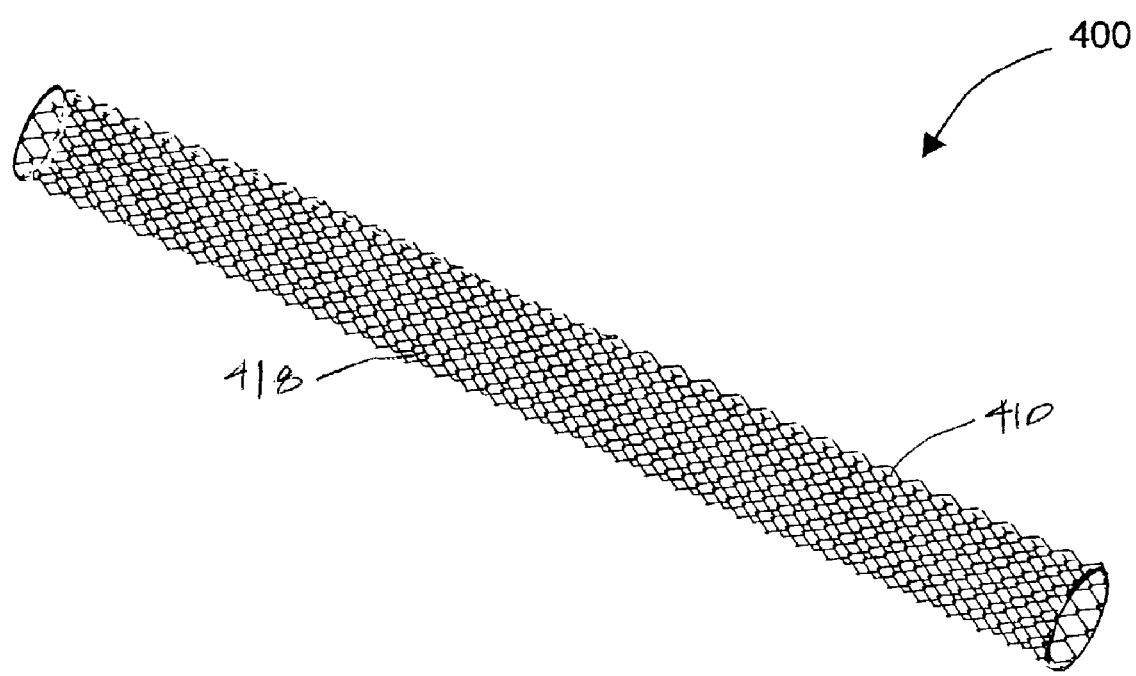
FIG. 11 is a perspective view of a Type "D" vaso-occlusive system that comprises a polymer sleeve having a mesh-like wall of woven filaments having a specified resistivity.
Figure 12:
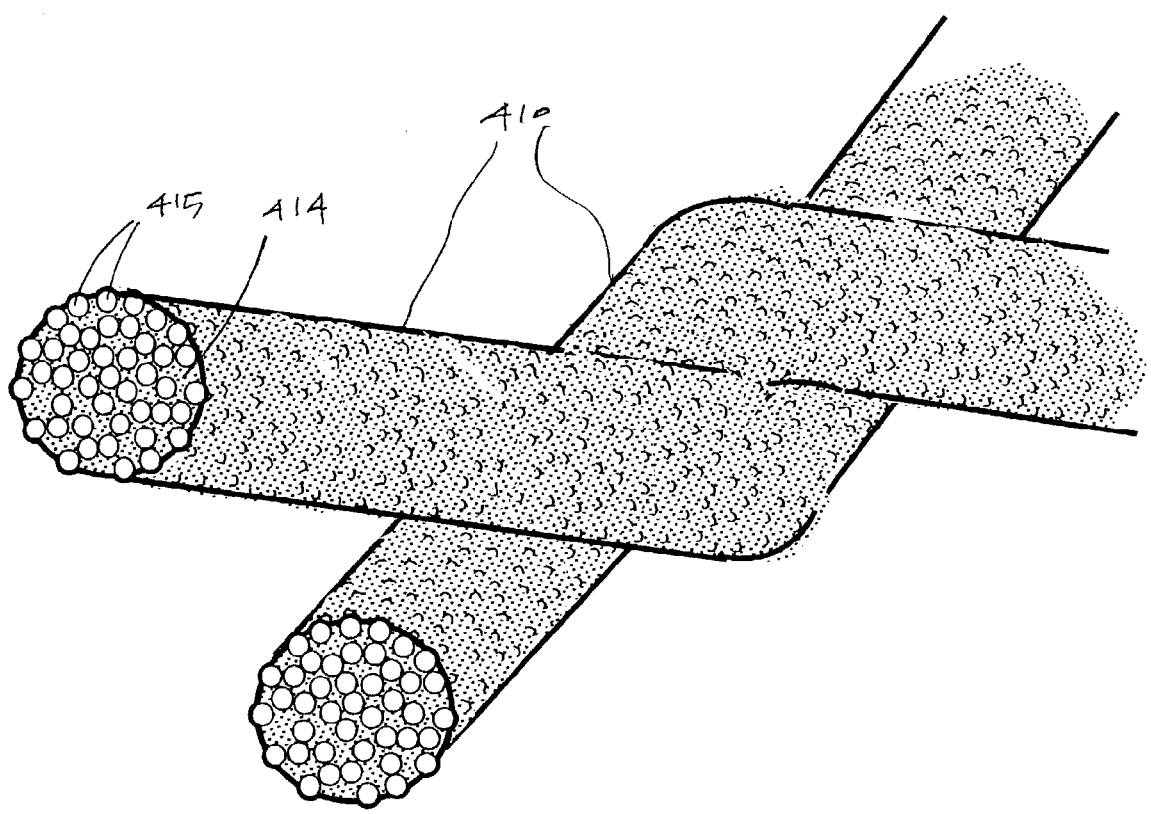
FIG. 12 is an enlarged view of the woven filaments of FIG. 11 depicting conductive particles therein.
Figure 13A:
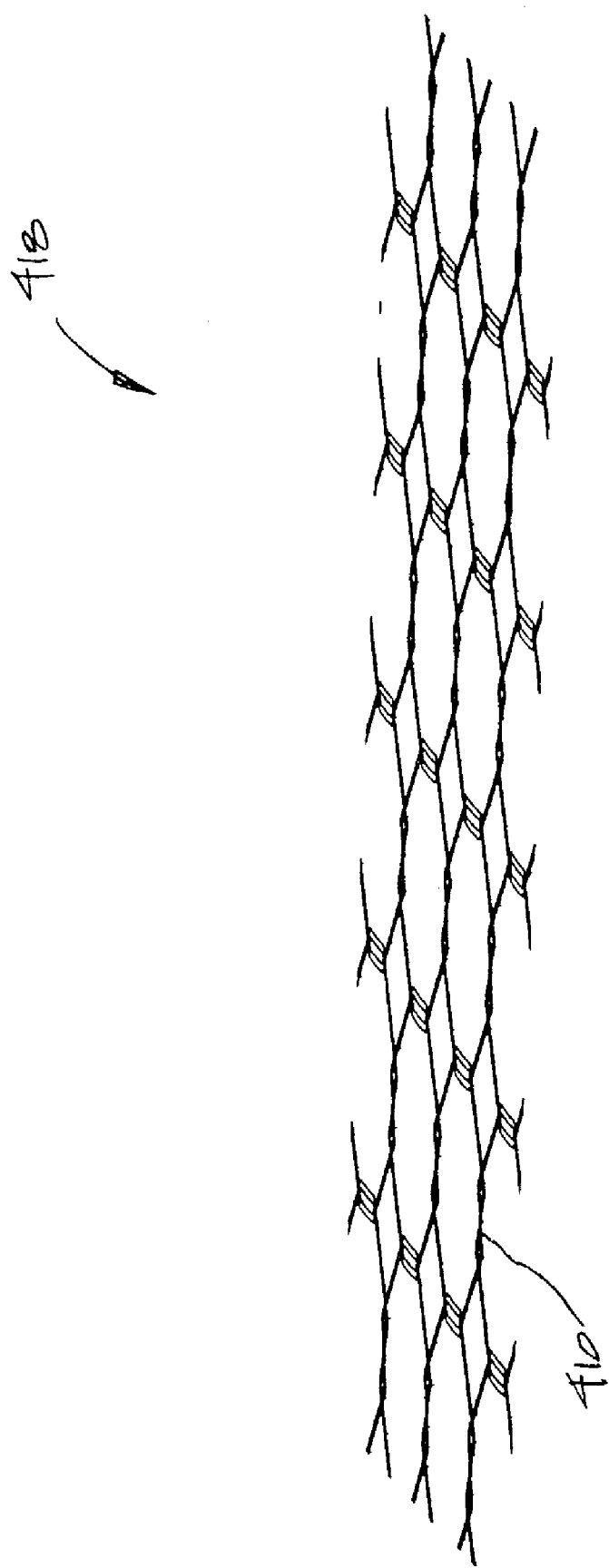
FIGS. 13A-13B are an enlarged views of the mesh-like wall of woven filaments of FIG. 11 showing non-expanded and expanded positions.
Figure 13B:
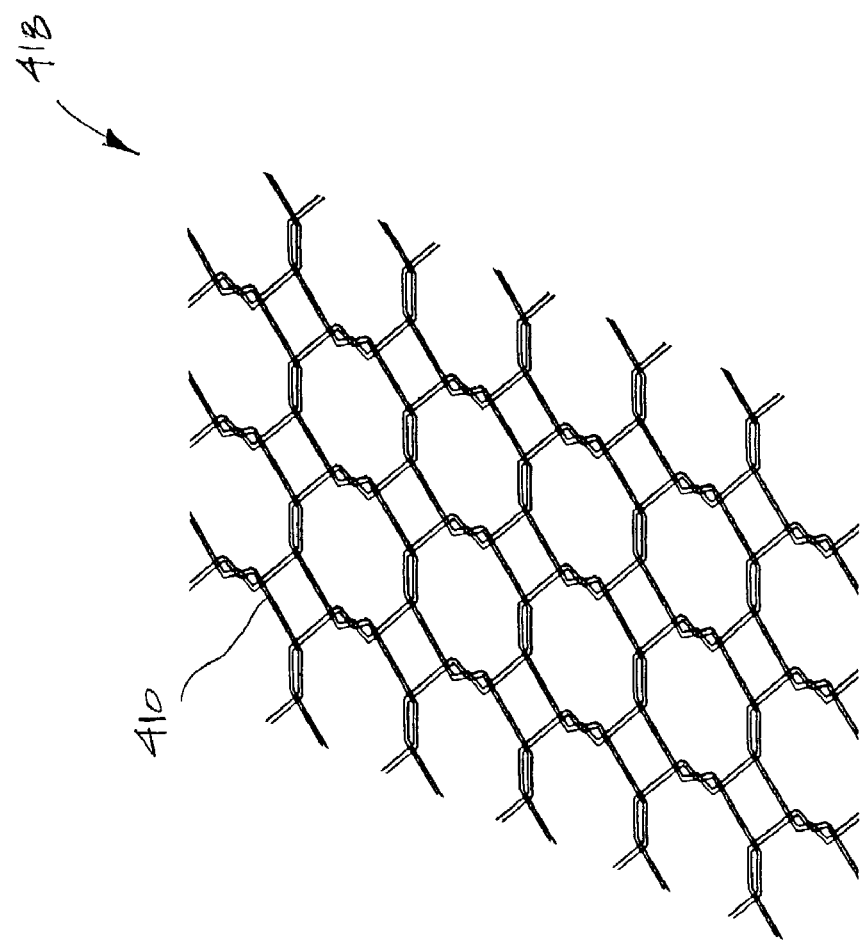

4. Type "D" embodiment of vaso-occlusive system. Referring to FIG. 11, the Type "D" vaso-occlusive system comprises a tubular sleeve 400 that is assembled or woven from a polymer filament 410 of the type that was described previously (see FIG. 10). The filament preferably is of the type illustrated (not-to-scale) in FIGS. 11-12 wherein the filament 410 comprises a first polymer portion 414 and a conductive portion 415. In one embodiment, the conductive portion 415 can comprise conductive particles such as carbon in a size ranging from about 1 nm to 10 microns. The conductive portion 415 alternatively can be any other conductive particle or filament of gold, silver or the like. The polymer filament 410 is then woven into a sleeve as depicted in FIG. 11 that can be moved between a first contracted cross-section and a second expanded cross-section. FIGS. 13A-13B depicts that woven wall structure 418 of the sleeve 400 as it is expanded from the first position (FIG. 13A) to the second position (FIG. 13B). The polymer filament 410 can have any suitable diameter ranging from about 0.0005" to 0.005". The polymer filament 410 also can of the type described in the Type "A" embodiment above wherein the polymer filament is made conductive by means of a very thin metallic coating.

The diameter of the filament 410 can be any suitable dimension to provide a sleeve 400 with a selected overall diameter for adhering to the walls of a blood vessel. In use, the filament 410 is adapted to receive electrical energy from source 50 wherein the conductive polymer conductive-resistive matrix is designed with a specified resistivity within a particular temperature range that will heat the filament to a selected temperature. The selected temperature is adapted to fuse the filaments of the sleeve to the vessel wall, as will be described next. The characteristics and features of the conductive polymer matrix corresponding to the invention are described in detail in co-pending Provisional U.S. Patent Application Ser. No. 60/366,992 filed Mar. 20, 2002 titled Electrosurgical Instrument and Method of Use, which is incorporated herein by reference. In co-pending Ser. No. 60/366,992, a conductive polymer matrix is disclosed for controllably delivering energy to tissue for purpose of tissue welding or tissue sealing, which is somewhat similar to the objectives of the present invention. The method of the present invention involves bonding a filament to tissue with the controlled application of electrical energy, which can rely on the positive temperature coefficient characteristics described in detail in co-pending Ser. No. 60/366, 992.

Figure 14A:
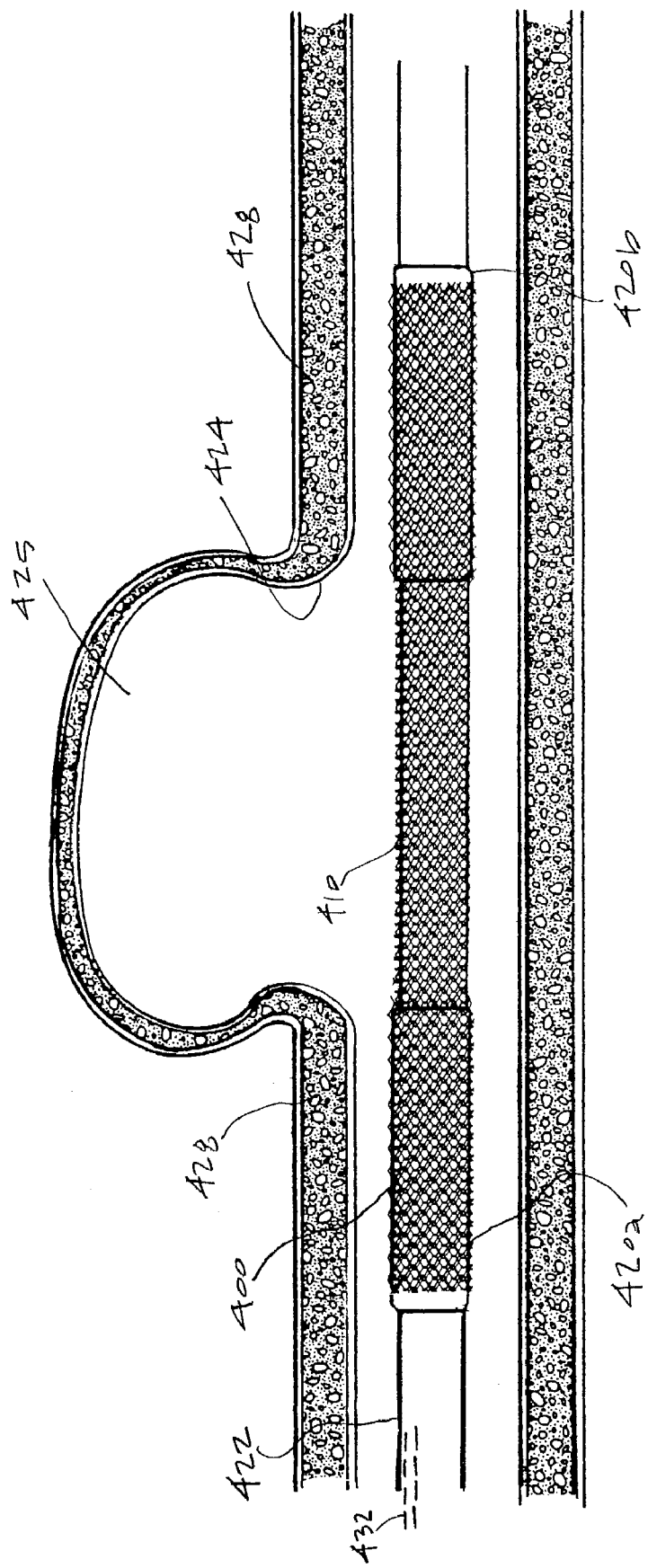
Figure 14B:
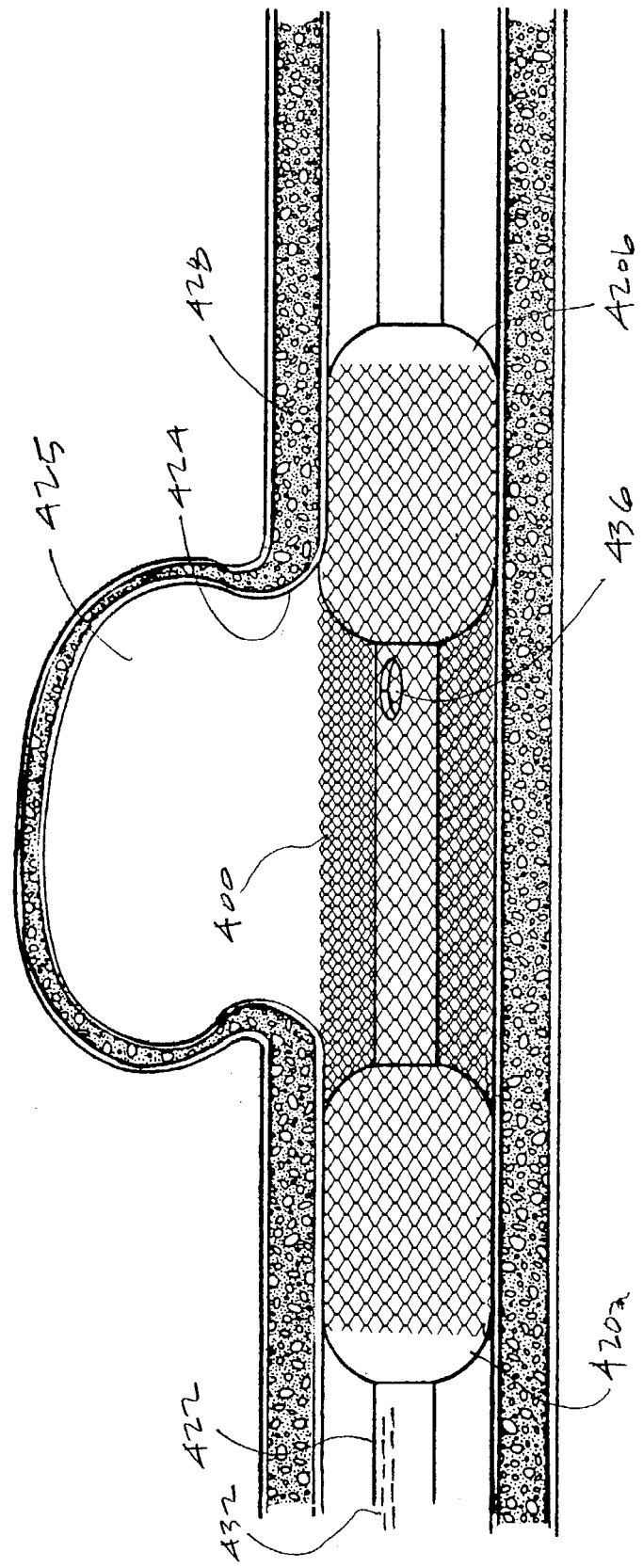
Figure 14C:
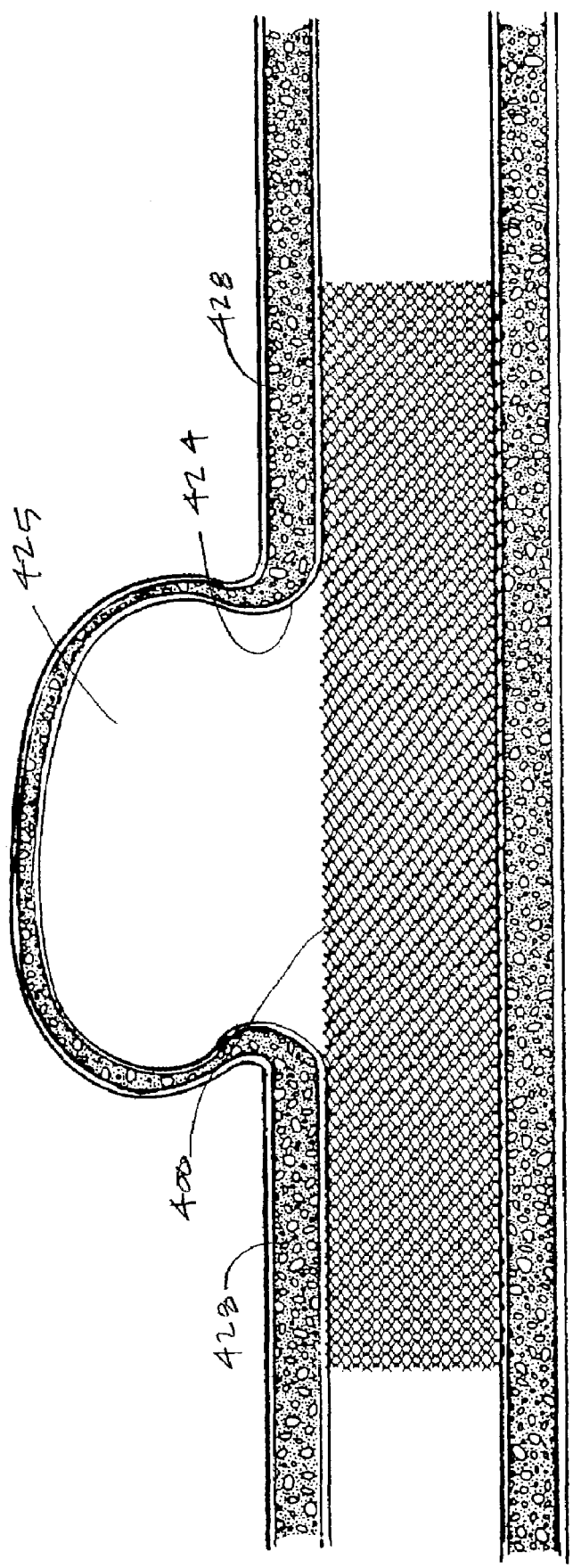

FIGS. 14A-14C next graphically depict the manner of using the polymer matrix sleeve 400 to treat a vascular malformation. The polymer filament sleeve 400 of FIG. 11 is particularly designed for treatment of wide-neck aneurysms, some-times referred to as "top-hat" aneurysms. Such malformations are often difficult to treat with embolic coils or other embolic filler materials since the vaso-occlusive materials may not be stable within the aneurysm sac. The polymer filament sleeve 400 is thus adapted to extend across the neck of aneurysm and thereafter be instantaneously fused to the vessel wall with the application of electrical energy. The filament sleeve 400 differs markedly from a conventional stent since the polymer sleeve is flexible, has an extremely thin wall dimension and becomes fused to the vessel wall for maintaining its position. In contrast, a stent is not flexible which leads to constant trauma to the vessel wall as it slightly changes in dimension as the vessel wall expands and contracts during the pulses of blood flow therethrough. Further, the stent remains in position only because of its expanded strength that pushes against the vessel wall.

FIG. 14A shows the polymer filament sleeve 400 is an assembly being disposed over first and second expandable balloons 420a and 420b at the working end of an elongate flexible introducer member 422. The sleeve 400 also can be carried over a single balloon member or any other type of expansion structure. In FIG. 14A, the sleeve 400 is positioned across the large open neck 424 of an exemplary aneurysm 425 in vessel wall 428. The introducer member 422 and at least one balloon can carry any suitable markings for cooperating with an imaging system.

FIG. 14B next illustrates the expansion of the balloons 420a and 420b that presses the woven wall structure 418 of the sleeve 400 against the walls 428 of the vessel. At least one inflation lumen 432 extends through the introducer member 422 to a pressure source as is known in the art.

Still referring to FIG. 14B, after the sleeve 400 is in an expanded or deployed position against the vessel walls, the electrical source 50 is actuated to deliver electrical current to the conductive filaments 410 of sleeve 400. The very fine filaments 410 can be elevated to a selected temperature of between about 60° C. and 90° C. for an interval ranging from about 0.01 second to 5.0 seconds which will fuse the filaments to the vessel wall 428. Preferably, the time interval of energy delivery is less that about 1.0 second. The very rapid energy delivery to the small cross-section filaments will prevent any substantial damage to the vessel walls.

FIG. 14C illustrates the sleeve 400 deployed and fused to the vessel walls after collapse of the balloons and withdrawal of the introducer member. The use of the polymer sleeve 400 alone can serve as a complete treatment for some types of aneurysms as the wall 418 of the sleeve that extends across the neck 424 of the aneurysm will cause a significant reduction in blood flow into and around the aneurysm which will lead to thrombosis in the aneurysm sac 425.

It should be appreciated that another sleeve 400 (not shown) can have a less porous central wall portion that extends across the neck 424 of the aneurysm to more effectively prevent blood flow into the aneurysm sac 425.

In another manner of practicing the invention, an embolic material may be introduced into the aneurysm sac 425 following deployment of the polymer sleeve 400 across the neck 424 of the aneurysm. Thus, the polymer sleeve 400 then can function as a mesh to retain the embolic material within a wide-neck aneurysm. The embolic material can be of any type known in the art, such as embolic coils, foams or liquid agents that can be cured or solidified within the aneurysm sac 425. FIG. 14B illustrates that the introducer 422 itself can have a port 436 for introducing embolic material into the aneurysm while the balloons are expanded and stabilizing the sleeve 400 across the neck 424 of the aneurysm.

The electrode connection between the introducer 422 and the sleeve 400 can be on the surfaces of the balloons or within the distal end of a bore that extends about the proximal end of the polymer sleeve 400. The polymer sleeve 400 thus can be an independent member in contact with an electrode or the sleeve can detach from a connection to the introducer member by the fuse-type means described previously. The system can operate with any type and location of return electrode.

Those skilled in the art will appreciate that the exemplary embodiments and descriptions of the invention herein are merely illustrative of the invention as a whole. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only being the true purview, spirit and scope of the invention.

What is claimed is:

1. An electrosurgical system for controlled application of energy to tissue, comprising:
    a flexible matrix material defining an engagement surface for contacting body media;
    the matrix material comprising a first portion and a second portion each in a selected proportion of the matrix volume;
    said first portion being an electrically non-conductive material;
    said second portion being electrically conductive and distributed within the first portion; and
    an electrical conductor coupled to said matrix material;
    wherein the first portion forms a matrix substantially throughout the volume enveloped within the engagement surface, wherein the second portion comprises conductive particles having a dimension across a principal axis ranging between about 1 nanometer and 100 microns.

2. The electrosurgical system of claim 1 wherein said first portion is a polymer.

3. The electrosurgical system of claim 1 wherein said first portion is an elastomeric material.

4. The electrosurgical system of claim 1 wherein the material defines a positively-sloped temperature-resistance curve over a selected temperature range.

5. The electro surgical system of claim 1 wherein the second portion is a conductive material selected from the group consisting of gold, platinum, silver, palladium, tin, tantalum, titanium, copper or combinations thereof.

6. The electrosurgical system of claim 1 wherein the first portion is of a material selected from the group consisting of nylon, PET, polyamide, aramid fiber, urethane or Kevlar™.

7. The system of claim 1, further comprising a sleeve configured to deliver the matrix material from a proximal end to a distal end thereof.

8. The system of claim 7, further comprising at least one electrode in the sleeve distal end with a single polarity.

9. The system of claim 7, further comprising first and second spaced apart electrodes with opposing polarities in the sleeve working end.

10. The system of claim 1, wherein the flexible matrix material forms a coagulum upon application of energy to the electrical conductor.

11. A system for treating a tissue, comprising:
    a polymer matrix carrying a conductive material at least partially distributed therein;
    a sleeve that releasably carries the polymer matrix from a proximal end to a distal working end thereof;
    a conductive electrode surface exposed about the distal working end proximate to the polymer matrix, wherein the polymer matrix includes conductive particles carried therein; and
    a remote electrical source coupled to said conductive electrode surface.

12. The system of claim 11, wherein the electrical source delivers electrical energy in the radiofrequency range.

13. The system of claim 11, wherein the polymer matrix carrying a conductive material is adapted to form a coagulum upon application of electrical energy from the remote electrical source.

14. The system of claim 11, further comprising at least one electrode in the sleeve distal working end with a single polarity.

15. The system of claim 11, further comprising first and second spaced apart electrodes with opposing polarities in the sleeve distal working end.

16. The system of claim 11, further comprising a slidable extension member within the sleeve for pushing the polymer matrix from the distal end of the sleeve.

17. The system of claim 11, wherein the tissue comprises vascular tissue.

18. A system for filling a volume within a patient's body, comprising:
   a matrix comprising an elastomer and a conductive material;
   a sleeve having a proximal end and a distal end, wherein at least one electrode is present about a distal portion of the sleeve, and wherein the sleeve defines a lumen which releasably carries the matrix from a proximal end to a distal end thereof; and
   a remote electrical source in electrical communication with the electrode;
   wherein the sleeve is configured to deploy the matrix into a patient's body adjacent body tissue; and
   wherein application of electrical energy from the remote electrical source to the matrix causes formation of a coagulum about the deployed matrix.

19. The system of claim 18, wherein the coagulum is at least partially formed within the volume occupied by the deployed matrix.

20. The system of claim 18, wherein the sleeve is configured to deploy the matrix in a patient's vasculature.

21. The system of claim 18, wherein the sleeve is configured to deploy the matrix in an aneurysm.

22. The system of claim 18, wherein the matrix includes conductive particles embedded therein.

23. The system of claim 18, wherein the electrical source delivers electrical energy in the radiofrequency range.

24. The system of claim 18, further comprising at least one electrode in the sleeve distal end with a single polarity.

25. The system of claim 18, further comprising first and second spaced apart electrodes with opposing polarities in the sleeve distal end.

* * * * *

UNITED STATES PATENT AND TRADEMARK OFFICE
CERTIFICATE OF CORRECTION

PATENT NO. : 7,306,598 B2 Page 1 of 1
APPLICATION NO. : 10/456113
DATED : December 11, 2007
INVENTOR(S) : Csaba Truckai et al.

It is certified that error appears in the above-identified patent and that said Letters Patent is hereby corrected as shown below:

Column 1, line 48, please delete "Gugliemli;" and insert --Guglielmi,--, therefor.

Column 1, line 51, please delete "Gugliemli;" and insert --Guglielmi,--, therefor.

Column 2, line 9, please delete "Gugliemli;" and insert --Guglielmi,--, therefor.

Column 4, line 24 (approx.), after "the" please delete "a".

Column 9, line 14, please delete "ie.," and insert --i.e.,--, therefor.

Column 10, line 2, after "15" please delete "wafts" and insert --watts,--, therefor.

Column 10, line 16, before "or;" please delete "(".

Column 10, line 26, please delete "ie.," and insert --i.e.,--, therefor.

Column 11, line 28, after "the" please delete "a".

Column 13, line 5, please delete "cf" and insert --cf.,--, therefor.

(Claims), column 16, line 27, In Claim 5, please delete "electro surgical" and insert --electrosurgical--, therefor.

Signed and Sealed this

Twenty-second Day of July, 2008

JON W. DUDAS
*Director of the United States Patent and Trademark Office*